(12) United States Patent
Takahashi et al.

(10) Patent No.: US 11,898,163 B2
(45) Date of Patent: Feb. 13, 2024

(54) METHOD FOR PRODUCING DOPAMINERGIC NEURON PROGENITOR CELL

(71) Applicants: KYOTO UNIVERSITY, Kyoto (JP); Sumitomo Pharma Co., Ltd., Osaka (JP)

(72) Inventors: Jun Takahashi, Kyoto (JP); Daisuke Doi, Kyoto (JP); Kenji Yoshida, Kobe (JP); Atsushi Kuwahara, Kobe (JP); Masayo Takahashi, Wako (JP)

(73) Assignees: KYOTO UNIVERSITY, Kyoto (JP); SUMITOMO PHARMA CO., LTD., Osaka (JP)

( * ) Notice: Subject to any disclaimer, the term of this patent is extended or adjusted under 35 U.S.C. 154(b) by 296 days.

(21) Appl. No.: 16/095,092

(22) PCT Filed: Apr. 24, 2017

(86) PCT No.: PCT/JP2017/016246
§ 371 (c)(1),
(2) Date: Oct. 19, 2018

(87) PCT Pub. No.: WO2017/183736
PCT Pub. Date: Oct. 26, 2017

(65) Prior Publication Data
US 2019/0112575 A1    Apr. 18, 2019

(30) Foreign Application Priority Data

Apr. 22, 2016  (JP) .............................. 2016-086499

(51) Int. Cl.
*C12N 5/0793* (2010.01)
*A61K 35/30* (2015.01)
*C12N 5/074* (2010.01)

(52) U.S. Cl.
CPC ............ *C12N 5/0619* (2013.01); *A61K 35/30* (2013.01); *C12N 5/0696* (2013.01); *C12N 2500/38* (2013.01); *C12N 2501/115* (2013.01); *C12N 2501/119* (2013.01); *C12N 2501/13* (2013.01); *C12N 2501/15* (2013.01); *C12N 2501/155* (2013.01); *C12N 2501/41* (2013.01); *C12N 2501/727* (2013.01); *C12N 2501/999* (2013.01); *C12N 2506/45* (2013.01); *C12N 2533/90* (2013.01)

(58) Field of Classification Search
None
See application file for complete search history.

(56) References Cited

U.S. PATENT DOCUMENTS

2006/0211109 A1   9/2006  Totey et al.
2007/0254281 A1  11/2007  Ono et al.
2008/0199437 A1   8/2008  Sakamoto et al.
2011/0008769 A1   1/2011  Ono et al.
2011/0217774 A1   9/2011  Kim et al.
2012/0178083 A1   7/2012  Ono et al.
2012/0252021 A1  10/2012  Ono et al.
2014/0193836 A1   7/2014  Takahashi et al.
2015/0299654 A1  10/2015  Sakamoto et al.
2016/0215260 A1*  7/2016  Takahashi ............ C12N 5/0619
2017/0313976 A1  11/2017  Kuwahara et al.
2017/0313981 A1  11/2017  Kuwahara et al.

FOREIGN PATENT DOCUMENTS

| JP | 2006-521807 A | 9/2006 | |
|---|---|---|---|
| JP | 2014-523734 A | 9/2014 | |
| JP | WO2015/034012 A1 | 3/2015 | |
| KR | 10-2011-0050310 A | 5/2011 | |
| WO | WO 2005/052190 A1 | 6/2005 | |
| WO | WO 2006/009241 A1 | 1/2006 | |
| WO | WO 2007/119759 A1 | 10/2007 | |
| WO | WO 2012/135621 A2 | 10/2012 | |
| WO | WO 2012/162124 A1 | 11/2012 | |
| WO | WO 2013/015457 A1 | 1/2013 | |
| WO | WO-2015034012 A1 * | 3/2015 | .............. A61P 25/16 |

(Continued)

OTHER PUBLICATIONS

Kirkeby et al Translational Neuroscience • 3(4) • 2012 • 314-319 (Year: 2012).*
Doi et al Stem Cell Reportss , 2, 337-350 (Year: 2014).*
Atkinson et al British Journal of Pharmacology 169, 269-289 (Year: 2013).*
Zhang Stem Cells Dev. 13(4):372-81 (Year: 2004).*
Li et al Nat Biotechnol. Feb;23(2):215-21 (Year: 2005).*
Yan et al Biomaterials, 73, 231-242 (Year: 2015).*
Doi et al Stem Cell Reports, 337-350 (Year: 2014).*
Wu et al Stem Cell Research 4, 38-49) (Year: 2010).*
Kriks et al (Nature , 480, 547-551 (Year: 2011).*
Wang et al Cells, 9(6), 1-26 (Year: 2020).*
Smidt et al Nat. Rev. Neurosci. 8, 21-32 (Year: 2007).*
Zhang et al Sci. Signal. 10, eaal4165 , 1-11 (Year: 2017).*
Wang et al Cell 9(6) 1-20 (Year: 2020).*
Smidt et al Nat Rev Neuroscience, 8, 21-32 (Year: 2007).*

(Continued)

*Primary Examiner* — Anoop K Singh
(74) *Attorney, Agent, or Firm* — Oblon, McClelland, Maier & Neustadt, L.L.P.

(57) ABSTRACT

A cell population comprising Corin- and/or Lrtm1-positive cells was produced by the following steps (1) and (2), from which Corin positive and/or Lrtm1 positive cells are collected using a substance that binds to Corin and/or a substance that binds to Lrtm1, and dopaminergic neuron progenitor cells are produced by performing suspension culture of the Corin positive and/or Lrtm1 positive cells in a culture solution containing one or more nutritional factors:
(1) a step of performing adhesion culture of pluripotent stem cells in a medium for maintaining undifferentiated state containing a Sonic hedgehog (SHH) signal stimulant, and an undifferentiated state-maintaining factor in the absence of feeder cells but in the presence of an extracellular matrix, and
(2) a step of culturing the cell population obtained in the step (1) in a culture solution containing one or more differentiation-inducing factors.

12 Claims, 4 Drawing Sheets

Specification includes a Sequence Listing.

(56) References Cited

FOREIGN PATENT DOCUMENTS

| WO | WO 2016/063985 A1 | 4/2016 |
| WO | WO 2016/063986 A1 | 4/2016 |

OTHER PUBLICATIONS

Thomas C. Schulz, et al., Differentiation of Human Embryonic Stem Cells to Dopaminergic Neurons in Serum-Free Suspension Culture, Stem Cells, vol. 22, 2004, pp. 1218-1238.

Hwang, et al., "Human ES and iPS Cells as Cell Sources for the Treatment of Parkinson's Disease: Current State and Problems", Journal of Cellular Biochemistry, vol. 109, 2010, pp. 292-301.

Jönsson, M.E., et al., "Identification of transplantable dopamine neuron precursors at different stages of midbrain neurogenesis", Experimental Neurology, vol. 219, 2009, pp. 341-354.

Miyazaki, T., et al., "Laminin E8 fragments support efficient adhesion an dexpansion ofdissociated human pluripotent stem cells", Nature Communications, vol. 3 No. 1236, 2012, pp. 1-10.

Samata, B., et al., "Purification of functional human ES and iPSC-derived midbrain dopaminergic progenitors using LRTM1", Nature Communications, vol. 7 No. 13097, 2016, pp 1-11.

Kirkeby, A., et al., "Generating regionalized neuronal cells from pluripotency, a step-by-step protocol", Frontiers in Cellular Neuroscience, vol. 6 article 64, 2013, pp. 1-4.

International Search Report dated Jul. 18, 2017 in PCT/JP2017/016246 filed Apr. 24, 2017.

Wernig, M. et al., "Neurons derived from reprogrammed fibroblasts functionally integrate into the fetal brain and improve symptoms of rats with Parkinson's disease," Proceedings ofthe National Academy of Sciences ofthe United States of America, vol. 105, No. 15, 2008, pp. 5856-5861.

Doi, D. et al., "Isolation of Human Induced Pluripotent Stem Cell-Derived Dopaminergic Progenitors by Cell Sorting for Successful Transplantation," Stem Cell Reports, vol. 2, No. 3, 2014, pp. 337-350.

Zhang, P. et al., "Directed Dopaminergic Neuron Differentiation from Human Pluripotent Stem Cells," Journal of Visualized Experiments, vol. 15, No. 91, 2014, pp. 1-8.

Xi, J. et al., "Specification of Midbrain Dopamine Neurons from Primate Pluripotent Stem Cells," Stem Cells, vol. 30, No. 8, 2012, pp. 1655-1663, 10 pages total.

English translation of the International Preliminary Report on patentability and Written Opinion dated Nov. 1, 2018 in PCT/JP2017/016246.

Zheng, K. et al. "Comparison of Different Culture Mode for Long-term Expansion of Neural Stem Cells", Dalian University of Technology, 2005, 76 pages (with partial English translation).

Tao, S. "Biological characteristics of neural precursor cells cultured by suspension and adherence methods and influence of ethanol on the expression of connexin-43 in neural precursor cells" Shandong University Master's Thesis, 2009, 67 pages (with partial English translation).

Bonnie J. Berry, et al, Advances and Current Challenges Associated with the Use of Human Induced Pluripotent Stem Cells in Modeling Neurodegenerative Disease; Cells Tissues Organs 2018; vol. 205:pp. 331-349.

Sushrut Dakhore, et al., Human Pluripotent Stem Cell Culture: Current Status, Challenges, and Advancement; Stem Cells International, vol. 2018, Article ID 7396905, 17 pages.

Shun Shibata, et al., "Selective Laminin-Directed Differentiation of Human Induced Pluripotent Stem Cells into Distinct Ocular Lineages", Cell Reports, vol. 25, 2018, pp. 1668-1679.

Sebastien Sart, et al., "Downstream bioprocessing of human pluripotent stem cell-derived therapeutics", Engineering in Life Sciences, 2021, pp. 1-14.

Ana Sofia Correia, et al., "Stem cell-based therapy for Parkinson's disease"; Annals of Medicine. 2005; 37: 487-498.

Yoshikawa, T., et al., "Systemic administration of valproic acid and zonisamide promotes differentiation of induced pluripotent stem cell-derived dopaminergic neurons", Frontiers in Cellular Neuroscience, vol. 7, article 11, 2013, pp. 1-10.

Doi. D., et al., "Prolonged Maturation Culture Favors a Reduction in the Tumorigenicity and the Dopaminergic Function of Human ESC-Derived Neural Cells in a Primate Model of Parkinson's Disease", Stem Cells, vol. 30, No. 5, 2012, pp. 935-945.

\* cited by examiner

SEQUENCE LISTING

```
<160> NUMBER OF SEQ ID NOS: 1

<210> SEQ ID NO 1
<211> LENGTH: 12
<212> TYPE: PRT
<213> ORGANISM: Artificial Sequence
<220> FEATURE:
<223> OTHER INFORMATION: L803-mts
<220> FEATURE:
<221> NAME/KEY: LIPID
<222> LOCATION: (1)..(1)
<223> OTHER INFORMATION: MYRISTATE
<220> FEATURE:
<221> NAME/KEY: MOD_RES
<222> LOCATION: (11)..(11)
<223> OTHER INFORMATION: PHOSPHORYLATION
<220> FEATURE:
<221> NAME/KEY: MOD_RES
<222> LOCATION: (12)..(12)
<223> OTHER INFORMATION: AMIDATION

<400> SEQUENCE: 1

Gly Lys Glu Ala Pro Pro Ala Pro Pro Gln Ser Pro
1               5                   10
```

METHOD FOR PRODUCING DOPAMINERGIC NEURON PROGENITOR CELL

TECHNICAL FIELD

The present invention relates to a method for producing dopaminergic neuron progenitor cells, and a method for producing a cell population comprising Corin positive and/or Lrtm1positive cells, which can be differentiated into dopaminergic neuron progenitor cells.

BACKGROUND ART

Parkinson's disease is a neurodegenerative disease caused by loss of dopaminergic neuron cells in the mesencephalic substantia nigra, and about 4 million people in the world are currently suffering from this disease. For treatment of Parkinson's disease, pharmacotherapy with L-DOPA or a dopamine agonist; coagulation by stereotaxy or deep brain stimulation; fetal mesencephalic grafting; or the like has been carried out.

Fetal mesencephalic grafting is problematic from an ethical point of view because of its source of supply, and the risk of infection is high in this treatment. Thus, a therapeutic method using neural cells prepared by differentiation induction from pluripotent stem cells such as embryonic stem cells (ES cells) or induced pluripotent stem cells (iPS cells) has been proposed (Non-patent Document 1). However, it has been pointed out that transplantation of neural cells prepared by differentiation induction may cause formation of a benign tumor, and dyskinesia which is thought to be due to cells other than the dopaminergic neural cells of interest. Therefore, selection of safe cells that can survive has been demanded for the transplantation.

As a method for producing dopaminergic neuron progenitor cells, a method including a step of selecting cells suitable for transplantation utilizing a gene that serves as a marker of dopaminergic neuron cells, or dopaminergic neuron progenitor cells has been proposed (Patent Literature 1). However, further improvement is required to reduce the influence of lot-to-lot variation due to inclusion of biological components, and to enhance production efficiency.

CITATION LIST

Patent Literature

[Patent Literature 1] WO 2015/34012

Non Patent Literature

[Non Patent Literature 1] Wernig M, et al., Proc Natl Acad Sci USA, 2008, 105: 5856-5861

SUMMARY OF INVENTION

Technical Problem

An object of the present invention is to produce dopaminergic neuron progenitor cells suitable for a therapeutic agent for Parkinson's disease. Therefore, one aspect of the present invention is to provide a method for producing dopaminergic neuron progenitor cells, and the like.

Solution to Problem

The present inventors made investigations to achieve the above object focusing attention on Corin and/or Lrtm1 that are cell surface membrane proteins and found a method for producing efficiently a cell population comprising cells that express such proteins. Further, the inventors also found that dopaminergic neuron progenitor cells can be obtained by extracting cells using Corin and/or Lrtm1 as an index from the cell population, and culturing the obtained cells, thereby completed the present invention.

The present invention includes the followings.

[1] A method for producing a cell population comprising Corin positive and/or Lrtm1 positive cells comprising the steps (1) and (2):
  (1) a step of performing adhesion culture of pluripotent stem cells in a medium for maintaining undifferentiated state containing a Sonic hedgehog (SHH) signal stimulant, and an undifferentiated state-maintaining factor in the absence of feeder cells but in the presence of an extracellular matrix, and
  (2) a step of culturing the cells obtained in Step (1) in a medium containing one or more differentiation-inducing factors.

[2] The producing method according to [1], wherein the SHH signal stimulant is SAG (N-methyl-N'-(3-pyridinylbenzyl)-N'-(3-chlorobenzo[b]thiophene-2-carbonyl)-1,4-diaminocyclohexane), shh protein or a fragment thereof, Purmorphamine, or a combination thereof.

[3] The producing method according to [1] or [2], wherein the medium for maintaining undifferentiated state in Step (1) further contains a TGF (Transforming Growth Factor)-β inhibitor, or a BMP (Bone Morphogenetic Protein) inhibitor.

[4] The producing method according to [3], wherein the TGFβ inhibitor is A83-01, and the BMP inhibitor is LDN 193189. [5] The producing method according to any one of [1] to [4], wherein the undifferentiated state-maintaining factor comprises at least one FGF (Fibroblast Growth Factor) signal transduction pathway agonist.

[6] The producing method according to [5], wherein the FGF signal transduction pathway agonist is bFGF.

[7] The producing method according to any one of [1] to [6], wherein the pluripotent stem cells are cultured for a period not exceeding 48 hours in Step (1).

[8] The producing method according to any one of [1] to [7], wherein the differentiation-inducing factor is one or more factors selected from the group consisting of a BMP inhibitor, a TGFβ inhibitor, an SHH signal stimulant, FGF8, and a GSK (Glycogen Synthase Kinase)-3β inhibitor.

[9] The producing method according to any one of [1] to [8], wherein Step (2) is a step of performing adhesion culture on an extracellular matrix.

[10] The producing method according to [9], wherein the extracellular matrix is laminin or a fragment thereof.

[11] The method according to [9], wherein the extracellular matrix is laminin-511 E8.

[12] The method according to any one of [1] to [11], wherein Step (2) comprises the following steps:
  (a) a step of performing adhesion culture of the cells obtained in Step (1) in a medium containing a BMP inhibitor and a TGFβ inhibitor in the presence of an extracellular matrix,
  (b) a step of performing adhesion culture of the cells obtained in Step (a) in a medium containing a BMP inhibitor, a TGFβ inhibitor, an SHH signal stimulant, and FGF8 in the presence of an extracellular matrix, (c) a step of performing adhesion culture of the cells obtained in Step (b) in a medium containing a BMP inhibitor, a TGFβ Inhibitor, an SHH signal stimulant, FGF8, and a GSK3β inhibitor in the presence of an extracellular matrix, and (d) a step of performing adhesion culture of the cells obtained in Step (c) in a medium containing a BMP inhibitor and a GSK3β inhibitor in the presence of an extracellular matrix.

[13] The producing method according to [12], wherein the medium in Step (a) further comprises a ROCK inhibitor.

[14] The producing method according to [13], wherein the ROCK inhibitor is Y-27632.

[15] The producing method according to any one of [12] to [14], wherein the BMP inhibitor in Step (2) is LDN 193189.

[16] The producing method according to any one of [12] to [15], wherein the TGFβ inhibitor in Step (2) is A83-01.

[17] The producing method according to any one of [12] to [16], wherein the SHH signal stimulant in Step (2) is Purmorphamine.

[18] The producing method according to any one of [12] to [17], wherein the GSK3β inhibitor is CHIR99021.

[19] The producing method according to any one of [1] to [18], wherein Step (2) is performed for at least 10 days.

[20] The producing method according to [19], wherein Step (2) is performed for 12 days to 21 days.

[21] The producing method according to [19], wherein Step (2) is performed for 12 days to 14 days.

[22] The producing method according to any one of [1] to [21], wherein the percentage of Corin positive and/or Lrtm1 positive cells contained in the cell population obtained after Step (2) is 10% or more.

[23] A method for producing dopaminergic neuron progenitor cells comprising the following steps:

(3) a step of collecting Corin positive and/or Lrtm1 positive cells from the cell population obtained by the producing method according to any one of [1] to [22] using a substance that binds to Corin and/or a substance that binds to Lrtm1, and (4) a step of performing suspension culture of the Corin positive and/or Lrtm1 positive cells obtained in Step (3) in a medium containing one or more neurotrophic factors.

[24] The producing method according to [23], wherein the substance that binds to Corin or the substance that binds to Lrtm1 is an antibody or aptamer that binds to Corin or Lrtm1

[25] The producing method according to [23] or [24], wherein the neurotrophic factors are BDNF and GDNF.

[26] The producing method according to any one of [23] to [25], wherein the medium containing a neurotrophic factor further contains B27 Supplement, ascorbic acid, and a cAMP analog.

[27] The producing method according to [26] above, wherein the cAMP analogue is Dibutyryl cyclic AMP.

[28] The producing method according to any one of [23] to [27] above, wherein the medium in Step (4) further contains a ROCK inhibitor.

[29] The producing method according to [28], wherein the ROCK inhibitor is Y-27632.

[30] The producing method according to any one of [23] to [29], wherein Step (4) is performed for at least 7 days.

[31] The producing method according to [30], wherein Step (4) is performed for 14 days to 30 days.

[32] The producing method according to [30], wherein Step (4) is performed for 14 days to 16 days.

[33] A cell population obtained by the producing method according to any one of [1] to [22], having the content of Corin positive and/or Lrtm1 positive cells of 10% or more.

[34] A dopaminergic neuron progenitor cell obtained by the producing method according to any one of [23] to [32].

[35] A therapeutic agent for Parkinson's disease comprising a dopaminergic neuron progenitor cell obtained by the producing method according to any one of [23] to [32].

Effects of Invention

According to the present invention, dopaminergic neuron progenitor cells useful for a therapeutic agent for Parkinson's disease, etc. can be efficiently obtained.

EMBODIMENTS FOR CARRYING OUT THE INVENTION

I. Definition

<Pluripotent Stem Cells>

Figure 1:
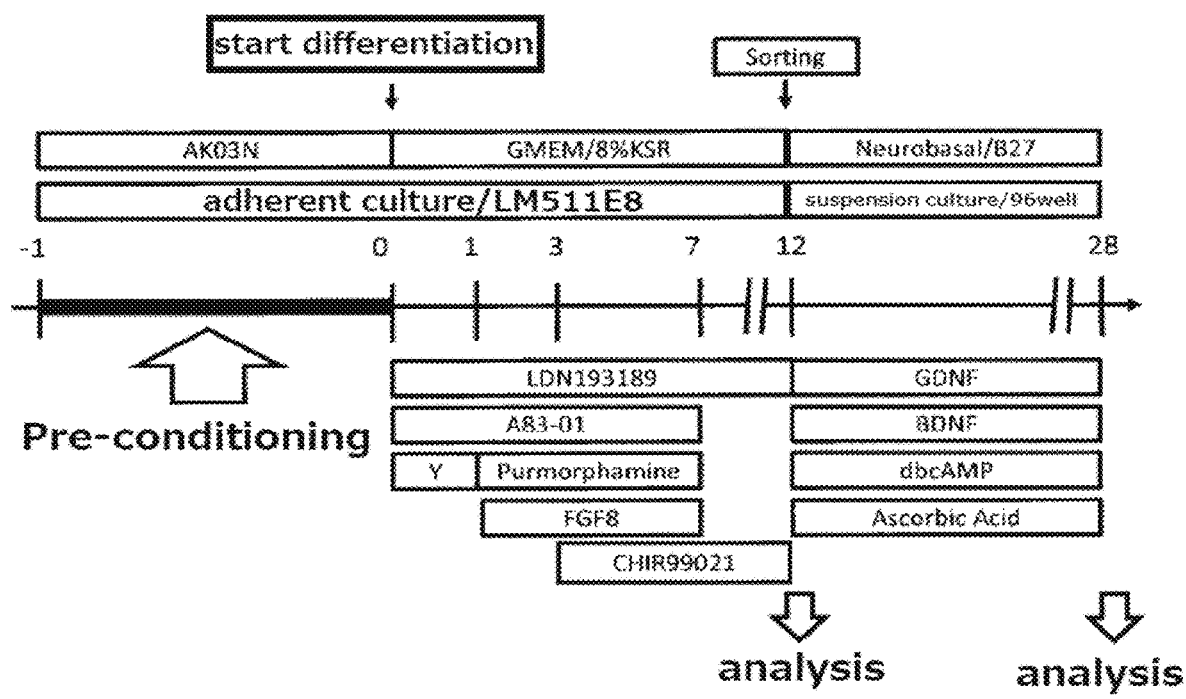
FIG. 1 shows an example of the protocol for producing dopamine-producing cells. In the figure, "Y" represents Y-27632.

The pluripotent stem cells which may be used in the present invention are stem cells having pluripotency which enables the cells to differentiate into any cells existing in the living body, which pluripotent stem cells also have growth ability. Examples of the pluripotent stem cells include, but are not limited to, embryonic stem (ES) cells, embryonic stem cells derived from a cloned embryo obtained by nuclear transfer (ntES cells), germline stem cells ("GS cells"), embryonic germ cells ("EG cells"), induced pluripotent stem (iPS) cells, and pluripotent cells derived from cultured fibroblasts and bone marrow stem cells (Muse cells). The pluripotent stem cells are preferably ES cells, ntES cells or iPS cells.

(A) Embryonic Stem Cells

ES cells are stem cells established from the inner cell mass of an early embryo (for example, blastocyst) of a mammal such as human or mouse, which cells have pluripotency and growth ability by self-renewal.

ES cells are embryo-derived stem cells originated from the inner cell mass of a blastocyst, which is the embryo formed following the 8-cell stage and the morula stage of a fertilized egg. ES cells have ability to differentiate into any cells constituting an adult, that is, the so-called pluripotency of differentiation, and growth ability by self-renewal. ES cells were discovered in mouse in 1981 (M. J. Evans, and M. H. Kaufman (1981), Nature 292: 154-156), and this was followed by establishment of ES cell lines of primates such as human and monkey (J. A. Thomson, et al. (1998), Science 282: 1145-1147; J. A. Thomson et al. (1995), Proc. Natl. Acad. Sci. USA, 92: 7844-7848; J. A. Thomson, et al. (1996), Biol. Reprod., 55: 254-259; J. A. Thomson, and V. S. Marshall (1998), Curr. Top. Dev. Biol., 38: 133-165).

ES cells can be established by removing the inner cell mass from the blastocyst of a fertilized egg of a subject animal, followed by culturing the inner cell mass on feeder fibroblasts. The cells can be maintained by subculture using a medium supplemented with substances such as leukemia inhibitory factor (LIF) and/or basic fibroblast growth factor (bFGF). Methods of establishment and maintenance of human and monkey ES cells are described in, for example, U.S. Pat. No. 5,843,780; Thomson J A, et al. (1995), Proc Natl. Acad. Sci. USA. 92:7844-7848; Thomson J A, et al. (1998), Science. 282: 1145-1147; H. Suemori et al. (2006), Biochem. Biophys. Res. Commun., 345: 926-932; M. Ueno et al. (2006), Proc. Natl. Acad. Sci. USA, 103: 9554-9559; H. Suemori et al. (2001), Dev. Dyn., 222: 273-279; H. Kawasaki et al. (2002), Proc. Natl. Acad. Sci. USA, 99: 1580-1585; and Klimanskaya I, et al. (2006), Nature. 444: 481-485.

In terms of the medium for preparation of ES cells, human ES cells can be maintained, for example, using DMEM/F-12 medium supplemented with 0.1 mM 2-mercaptoethanol, 0.1 mM non-essential amino acids, 2 mM L-glutamic acid, 20% KSR, and 4 ng/mL bFGF at 37° C. under a moist atmosphere of 2% $CO_2$/98% air (O. Fumitaka et al. (2008), Nat. Biotechnol., 26: 215-224). ES cells need to be subcultured every 3 to 4 days, and the subculture can be carried out using 0.25% trypsin and 0.1 mg/mL collagenase IV in PBS supplemented with 1 mM $CaCl_2$ and 20% KSR.

Selection of ES cells can be generally carried out by the Real-Time PCR method using as indices of marker gene expressions such as alkaline phosphatase, Oct-3/4, and/or Nanog. In particular, for selection of human ES cells, expression of a gene marker(s) such as OCT-3/4, NANOG and/or ECAD can be used as an index/indices (E. Kroon et al. (2008), Nat. Biotechnol., 26: 443-452).

In terms of human ES cell lines, for example, WA01(H1) and WA09(H9) can be obtained from WiCell Research Institute, and KhES-1, KhES-2, and KhES-3 can be obtained from Institute for Frontier Medical Sciences, Kyoto University (Kyoto, Japan).

(B) Germline Stem Cells

Germline stem cells are pluripotent stem cells derived from testis, and play a role as the origin for spermatogenesis. Similar to ES cells, these cells can be induced to differentiate into various series of cells, and, for example, have a property to enable preparation of a chimeric mouse by transplantation of the cells to a mouse blastocyst (M. Kanatsu-Shinohara et al. (2003) Biol. Reprod., 69: 612-616; K. Shinohara et al. (2004), Cell, 119: 1001-1012). Germline stem cells are capable of self-renewal in a medium containing glial cell line-derived neurotrophic factor (GDNF), and, by repeating subculture under the same culture conditions as those for ES cells, germline stem cells can be obtained (Masanori Takebayashi et al. (2008), Experimental Medicine, 26(5) (extra edition): 41-46, Yodosha (Tokyo, Japan)).

(C) Embryonic Germ Cells

Embryonic germ cells are established from fetal primordial germ cells and have pluripotency similarly to ES cells. They can be established by culturing primordial germ cells in the presence of substances such as LIF, bFGF, and stem cell factor (Y. Matsui et al. (1992), Cell, 70: 841-847; J. L. Resnick et al. (1992), Nature, 359: 550-551).

(D) Induced Pluripotent Stem Cells

Induced pluripotent stem (iPS) cells can be prepared by introducing specific reprogramming factors to somatic cells, which reprogramming factors are in the form of DNA or protein. iPS cells are somatic cell-derived artificial stem cells having properties almost equivalent to those of ES cells, such as pluripotency of differentiation and growth ability by self-renewal (K. Takahashi and S. Yamanaka (2006) Cell, 126: 663-676; K. Takahashi et al. (2007), Cell, 131: 861-872; J. Yu et al. (2007), Science, 318: 1917-1920; Nakagawa, M. et al., Nat. Biotechnol. 26: 101-106 (2008); WO 2007/069666, Okita, K., et al. Stem Cells 31, 458-66 (2013)). The reprogramming factors may be constituted by genes or gene products thereof, or non-coding RNAs, which are expressed specifically in ES cells; or genes or gene products thereof, non-coding RNAs, or low molecular weight compounds, which play important roles in maintenance of the undifferentiated state of ES cells. Examples of the genes included in the reprogramming factors include Oct3/4, Sox2, Sox1, Sox3, Sox15, Sox17, Klf4, Klf2, c-Myc, N-Myc, L-Myc, Nanog, Lin28, Fbx15, ERas, ECAT15-2, Tcl1, beta-catenin, Lin28 b, Sal11, Sal14, Esrrb, Nr5a2, Tbx3, dominant-negative form p53, an inhibitor of p53 gene such as shRNA, and EBNA1 or Glis1. These reprogramming factors may be used either singly or in combination. Examples of the combinations of the reprogramming factors include those described in WO 2007/069666; WO 2008/118820; WO 2009/007852; WO 2009/032194; WO 2009/058413; WO 2009/057831; WO 2009/075119; WO 2009/079007; WO 2009/091659; WO 2009/101084; WO 2009/101407; WO 2009/102983; WO 2009/114949; WO 2009/117439; WO 2009/126250; WO 2009/126251; WO 2009/126655; WO 2009/157593; WO 2010/009015; WO 2010/033906; WO 2010/033920; WO 2010/042800; WO 2010/050626; WO 2010/056831; WO 2010/068955; WO 2010/098419; WO 2010/102267; WO 2010/111409; WO 2010/111422; WO 2010/115050; WO 2010/124290; WO 2010/147395; WO 2010/147612; WO2011/16588; WO2013/176233; Huangfu D, et al. (2008), Nat. Biotechnol., 26: 795-797; Shi Y, et al. (2008), Cell Stem Cell, 2: 525-528; Eminli S, et al. (2008), Stem Cells. 26: 2467-2474; Huangfu D, et al. (2008), Nat Biotechnol. 26:

1269-1275; Shi Y, et al. (2008), Cell Stem Cell, 3, 568-574; Zhao Y, et al. (2008), Cell Stem Cell, 3: 475-479; Marson A, (2008), Cell Stem Cell, 3, 132-135; Feng B, et al. (2009), Nat Cell Biol. 11: 197-203; R. L. Judson et al., (2009), Nat. Biotech., 27: 459-461; Lyssiotis C A, et al. (2009), Proc Natl Acad Sci USA. 106: 8912-8917; Kim J B, et al. (2009), Nature. 461: 649-643; Ichida J K, et al. (2009), Cell Stem Cell. 5: 491-503; Heng J C, et al. (2010), Cell Stem Cell. 6: 167-74; Han J, et al. (2010), Nature. 463: 1096-100; Mali P, et al. (2010), Stem Cells. 28: 713-720; and Maekawa M, et al. (2011), Nature. 474: 225-9.

Examples of the above-described reprogramming factors also include histone deacetylase (HDAC) inhibitors [for example, low molecular weight inhibitors, such as valproic acid (VPA), trichostatin A, sodium butyrate, MC 1293, and M344; and nucleic acid-type expression inhibitors, such as siRNAs and shRNAs against HDAC (e.g., HDAC1 siRNA Smartpool (Millipore), and HuSH 29mer shRNA Constructs against HDAC1 (OriGene))], MEK inhibitors (for example, PD184352, PD98059, U0126, SL327, and PD0325901), glycogen synthase kinase-3 inhibitors (for example, Bio and CHIR99021), DNA methyltransferase inhibitors (for example, 5-azacytidine), histone methyltransferase inhibitors (for example, low molecular weight inhibitors such as BIX-01294, and nucleic acid-type expression inhibitors, such as siRNAs and shRNAs against Suv39h1, Suv39h2, SetDB1, and G9a), L-channel calcium agonists (for example, Bayk8644), butyric acid, TGFβ inhibitors or ALK5 inhibitors (for example, LY364947, SB431542, 616453, and A83-01), p53 inhibitors (for example, a dominant-negative form, siRNAs and shRNAs against p53), ARID3A inhibitors (for example, siRNAs and shRNAs against ARID3A), miRNAs such as miR-291-3p, miR-294, miR-295, and mir-302, Wnt Signaling (for example, soluble Wnt3a), neuropeptide Y, prostaglandins (for example, prostaglandin E2, and prostaglandin J2), hTERT, SV40LT, UTF1, IRX6, GLIS1, PITX2, and DMRTB1, which are employed for enhancing the establishment efficiency, and, in the present description, these factors employed for the purpose of enhancement of the establishment efficiency are not particularly distinguished from reprogramming factors. One or more of these may be appropriately selected and used.

In cases where the reprogramming factors are in the form of protein, the reprogramming factors may be introduced into somatic cells by a method, such as lipofection, fusion with a cell membrane-permeable peptide (e.g., HIV-derived TAT or polyarginine), or microinjection.

In cases where the reprogramming factors are in the form of DNA, the reprogramming factors may be introduced into somatic cells by a method, such as use of a vector including virus, plasmid, and artificial chromosome vectors; lipofection; use of liposome; or microinjection. Examples of the virus vectors include retrovirus vectors, lentivirus vectors (these are described in Cell, 126, pp. 663-676, 2006; Cell, 131, pp. 861-872, 2007; and Science, 318, pp. 1917-1920, 2007), adenovirus vectors (Science, 322, 945-949, 2008), adeno-associated virus vectors, and Sendai virus vectors (WO 2010/008054). Examples of the artificial chromosome vectors include human artificial chromosomes (HACs), yeast artificial chromosomes (YACs), and bacterial artificial chromosomes (BACs and PACs). As the plasmids, for example, plasmids for mammalian cells (Science, 322: 949-953, 2008) may be used. The vectors may contain a regulatory sequence(s) such as a promoter, enhancer, ribosome binding sequence, terminator, and/or polyadenylation site for allowing expression of the nuclear reprogramming substances; and, as required, a sequence of a selection marker such as a drug resistance gene (e.g., kanamycin-resistant gene, ampicillin-resistant gene, or puromycin-resistant gene), thymidine kinase gene, or diphtheria toxin gene; a gene sequence of a reporter, such as a green-fluorescent protein (GFP), β-glucuronidase (GUS), or FLAG; and/or the like. Further, in order to remove, after introduction of the above vector into somatic cells, the genes encoding the reprogramming factors, or both the promoters and the genes encoding the reprogramming factors linked thereto, the vector may have LoxP sequences upstream and downstream of these sequences.

In cases where the reprogramming factors are in the form of RNA, each reprogramming factor may be introduced into somatic cells by a method, such as lipofection, or microinjection, and RNA in which 5-methylcytidine and pseudouridine (TriLink Biotechnologies) are incorporated may be used in order to suppress degradation (Warren L, (2010) Cell Stem Cell. 7: 618-630).

Examples of the medium for induction of the iPS cells include DMEM, DMEM/F12, and DME media supplemented with 10 to 15% FBS (these media may further contain one or more of L1F, penicillin/streptomycin, puromycin, L-glutamine, non-essential amino acids, 2-mercaptoethanol, and the like, as appropriate); and commercially available media [for example, a medium for culturing mouse ES cells (TX-WES medium, Thromb-X), a medium for culturing primate ES cells (culture medium for primate ES/iPS cells, ReproCELL), and a serum-free medium (mTeSR, STEMCELL Technologies Inc.)].

Examples of the culture method include a method wherein somatic cells and reprogramming factors are brought into contact with each other at 37° C. in the presence of 5% $CO_2$ on DMEM or DMEM/F12 medium supplemented with 10% FBS, and the cells are cultured for about 4 to 7 days, followed by plating the cells on feeder cells (e.g., mitomycin C-treated STO cells or SNL cells) and starting culture in a bFGF-containing medium for culturing primate ES cells about 10 days after the contact between the somatic cells and the reprogramming factors, thereby allowing iPS-like colonies to appear about 30 to about 45 days after the contact, or later.

Alternatively, the cells may be cultured at 37° C. in the presence of 5% $CO_2$ on feeder cells (e.g., mitomycin C-treated STO cells or SNL cells) in DMEM medium supplemented with 10% FBS (this medium may further contain one or more of LIF, penicillin/streptomycin, puromycin, L-glutamine, non-essential amino acids, 2-mercaptoethanol, and the like, as appropriate) for about 25 to about 30 days or longer, to allow ES-like colonies to appear. Preferred examples of the culture method include a method wherein the somatic cells themselves to be reprogrammed are used instead of the feeder cells (Takahashi K, et al. (2009), PLoS One. 4: e8067 or WO 2010/137746), and a method wherein an extracellular matrix (e.g., Laminin-5 (WO 2009/123349), or BD Matrigel (BD Biosciences)) is used instead of the feeder cells.

Other examples of the culture method include a method wherein culture is carried out using a serum-free medium (Sun N, et al. (2009), Proc Natl Acad Sci USA. 106:15720-15725). Further, in order to enhance the establishment efficiency, iPS cells may be established under low oxygen conditions (at an oxygen concentration of 0.1% to 15%) (Yoshida Y, et al. (2009), Cell Stem Cell. 5:237-241 or WO 2010/013845).

During the culture, the medium is replaced with a fresh medium once every day from Day 2 of the culture. The number of the somatic cells used for nuclear reprogramming is not restricted, and usually within a range of about $5\times10^3$ to about $5\times10^6$ cells per 100 cm$^2$ of the culture dish.

iPS cells can be selected based on the shape of each formed colony. In cases where a drug resistance gene expressed in conjunction with a gene that is expressed upon reprogramming of a somatic cell (e.g., Oct3/4 or Nanog) is introduced as a marker gene, established iPS cells can be selected by culturing the cells in a medium containing the corresponding drug (selection medium). iPS cells can be selected by observation under a fluorescence microscope in cases where the marker gene is the gene of a fluorescent protein; by adding a luminescent substrate in cases where the marker gene is the gene of luciferase; or by adding a coloring substrate in cases where the marker gene is the gene of a coloring enzyme.

The term "somatic cells" used in the present description means any animal cells (preferably cells of mammals including human) excluding germ-line cells and totipotent cells such as eggs, oocytes, and ES cells. Examples of the somatic cells include, but are not limited to, any of fetal somatic cells, neonatal somatic cells, and mature, healthy and diseased somatic cells, as well as any of primary cultured cells, subcultured cells, and established cell lines. Specific examples of the somatic cells include (1) tissue stem cells (somatic stem cells), such as neural stem cells, hematopoietic stem cells, mesenchymal stem cells, and dental pulp stem cells; (2) tissue progenitor cells; and (3) differentiated cells, such as lymphocytes, epithelial cells, endothelial cells, muscle cells, fibroblasts (skin cells and the like), hair cells, hepatic cells, gastric mucosal cells, enterocytes, spleen cells, pancreatic cells (pancreatic exocrine cells and the like), brain cells, lung cells, kidney cells, and adipocytes.

In cases where iPS cells are used as a material for the cells to be transplanted, somatic cells whose HLA genotype is the same or substantially the same as that of the individual to which the cells are to be transplanted are preferably used in view of prevention of the rejection reaction. The term "substantially the same" herein means that the HLA genotype is matching to an extent at which the immune reaction against the transplanted cells can be suppressed with an immunosuppressive agent. For example, the somatic cells have matched HLA types at 3 loci HLA-A, HLA-B, and HLA-DR, or at the 4 loci further including HLA-C.

(E) ES Cells Derived from Cloned Embryo Obtained by Nuclear Transfer ntES cells are ES cells derived from a cloned embryo prepared by the nuclear transfer technique, and have almost the same properties as those of ES cells derived from fertilized eggs (T. Wakayama et al. (2001), Science, 292: 740-743; S. Wakayama et al. (2005), Biol. Reprod., 72: 932-936; J. Byrne et al. (2007), Nature, 450: 497-502). That is, an ntES (nuclear transfer ES) cell is an ES cell established from the inner cell mass of a blastocyst derived from a cloned embryo obtained by replacement of the nucleus of an unfertilized egg with the nucleus of a somatic cell. For preparation of an ntES cell, the combination of the nuclear transfer technique (J. B. Cibelli et al. (1998), Nature Biotechnol., 16: 642-646) and the ES cell preparation technique (described above) is employed (Sayaka Wakayama et al. (2008), Experimental Medicine 26 (5) (extra edition), pp. 47-52). In nuclear transfer, reprogramming can be achieved by injecting the nucleus of a somatic cell into a mammalian enucleated unfertilized egg and culturing the resultant for several hours.

(F) Multilineage-Differentiating Stress Enduring Cells (Muse Cells)

Muse cells are pluripotent stem cells produced by the method described in WO 2011/007900. More specifically, Muse cells are cells having pluripotency obtained by subjecting fibroblasts or bone marrow stromal cells to trypsin treatment for a long period, preferably to trypsin treatment for 8 hours or 16 hours, followed by suspension culture of the treated cells. Muse cells are positive for SSEA-3 and CD105.

<Dopaminergic Neuron Progenitor Cells>

In the present invention, the meaning of "dopaminergic neuron progenitor cells" may include dopamine producing neural cells, dopaminergic neurons, and the like, unless otherwise specified. The dopaminergic neuron progenitor cells may be a cell population containing other types of cells, however the cell population preferably does not contain a serotonin neural cell. The dopaminergic neuron progenitor cells are preferably a cell population containing Foxa2, Nurr1, Lmx1a, Pitx3, and/or TH-positive cells. In the present invention, examples of human Foxa2 include the polynucleotides of NCBI accession Nos. NM_021784 and NM_153675, and proteins encoded by these polynucleotides. In the present invention, examples of human Nurr1 include the polynucleotide of NCBI accession No. NM_006186, and proteins encoded by this polynucleotide. In the present invention, examples of human TH include the polynucleotides of NCBI accession Nos. NM_000360, NM_199292, and NM_199293, and proteins encoded by these polynucleotides. Examples of human Lmx1a include the polynucleotides of NCBI accession Nos. NM_001174069 and NM_177398, and proteins encoded by these polynucleotides. Examples of human Pitx3 include the polynucleotide of NCBI accession No. NM_005029, and proteins encoded by this polynucleotide.

<SHH Signal Stimulant>

The SHH (Sonic hedgehog) signal stimulant in the present invention is defined as a substance that causes disinhibition of Smoothened (Smo) due to binding of SHH to its receptor, Patched (Ptch1), and subsequent activation of Gli2. Examples thereof include proteins belonging to the Hedgehog family, specifically SHH, or IHH (Indian Hedgehog), SHH receptor, SHH receptor agonist, Hh-Ag1.5 (Li, X., et al., Nature Biotechnology, 23, 215-221 (2005), Smoothened Agonist, SAG (N-Methyl-N'-(3-pyridinylbenzyl)-N'-(3-chlorobenzo[b]thiophene-2-carbonyl)-1,4-diaminocyclohexane, 20a-hydroxycholesterol, Purmorphamine (PMA; 9-cyclohexyl-N-[4-(4-morpholinyl)phenyl]2-(1-naphth a1 enyl oxy)-9H-purin-6-amine), and derivatives thereof (Stanton B Z, Peng L F., Mol Biosyst. 6: 44-54, 2010). As an SHH signal stimulant, one, or two or more kinds of these may be appropriately selected and used.

Preferable examples of an SHH signal stimulant to be used in the present invention may include the Shh proteins (Genbank Accession Nos: NM_000193, and NP_000184), Purmorphamine, and SAG <Undifferentiated State-Maintaining Factor>

There is no particular restriction on an undifferentiated state-maintaining factor, insofar as it suppresses differentiation of pluripotent stem cells. In the case of primed pluripotent stem cells (for example, human ES cells, and human iPS cells), examples of an undifferentiated state-maintaining factor which is widely used by those skilled in the art may include an FGF signal transduction pathway agonist, a TGFβ agonist, and insulin. Specific examples of the FGF signal transduction pathway agonist may include a fibroblast growth factor (e.g. bFGF, FGF4, and FGF8). Examples of a TGFβ agonist include a TGFβ signal transduction pathway agonist, and a Nodal/Activin signal transduction pathway agonist. Examples of a TGFβ signal transduction pathway agonist include TGFβ1, and TGFβ2. Examples of a Nodal/Activin signal transduction pathway agonist include Nodal, Activin A, and Activin B. As undifferentiated state-maintaining factors, one, or two or more kinds thereof may be appropriately selected and used. When human pluripotent stem cells (human ES cells, or human iPS cells) are cultured, the medium in Step (1) preferably contains at least bFGF as an undifferentiated state-maintaining factor.

An undifferentiated state-maintaining factor to be used in the present invention is usually a mammalian undifferentiated state-maintaining factor.

The term mammal includes herein rodent, Ungulata, Carnivora, and primate. Rodent includes mouse, rat, hamster, and guinea pig. Ungulata includes pig, cow, goat, horse, and sheep. Carnivora includes dog, and cat. "Primate" means herein mammals belonging to Primates, and Primates includes Prosimiae, such as lemur, loris, and tree shrew, and Anthropoidea, such as monkey, anthropoid, and human.

Since an undifferentiated state-maintaining factor can have cross-reactivity among mammalian species, an undifferentiated state-maintaining factor of any mammal may be used, insofar as it can maintain the undifferentiated state of pluripotent stem cells to be cultured. It is preferable, however, that an undifferentiated state-maintaining factor of the same mammalian species as the cells to be cultured is used. For example, a human undifferentiated state-maintaining factor (such as bFGF, FGF 4, FGF8, EGF, Nodal, Activin A, Activin B, TGFβ1, and TGFβ2) is used for culturing human pluripotent stem cells. In this regard, the term "human protein X" means that a protein X has the amino acid sequence of the protein X that expresses naturally in a human living body.

An undifferentiated state-maintaining factor to be used in the present invention is preferably isolated. "Isolated" means a state out of a naturally occurring state as a result of performing an operation to remove factors other than an aimed ingredient or an aimed cell. Therefore, an "isolated protein X" does not include an endogenous protein X which is produced by cultured cells or tissues, and contained in the cells, tissues and a medium. The purity of an "isolated protein X" (the percentage of the weight of a protein X relative to the total protein weight) is usually 70% or more, preferably 80% or more, more preferably 90% or more, further preferably 99% or more, and still further preferably 100%. Thus, in an embodiment, the present invention includes a step of providing an isolated undifferentiated state-maintaining factor. Also, in one embodiment, the present invention includes a step of extrinsically (or exogenously) adding an isolated undifferentiated state-maintaining factor into a medium used in Step (1). Alternatively, an undifferentiated state-maintaining factor may be added in advance to a medium used in Step (1).

The concentration of an undifferentiated state-maintaining factor in a medium used in Step (1) is a concentration capable of maintaining the undifferentiated state of pluripotent stem cells to be cultured, which can be appropriately determined by those skilled in the art. Specifically, for example, when bFGF is used as the undifferentiated state-maintaining factor in the absence of feeder cells, the concentration is usually about 4 ng to 500 ng/mL, preferably about 10 ng to 200 ng/mL, and more preferably about 30 ng to 150 ng/mL.

<Medium>

A medium to be used for cell culture in the present invention may be prepared using a medium commonly used for culturing animal cells as a basal medium, or purchased commercially. Examples of a basal medium that can be used for animal cell culture may include BME medium, BGJb medium, CMRL 1066 medium, Glasgow MEM (GMEM) medium, Improved MEM Zinc Option medium, IMDM medium, Medium 199 medium, Eagle MEM medium, αMEM medium, DMEM medium, F12 medium, DMEM/F12 medium, IMDM/F12 medium, Ham's medium, RPMI 1640 medium, Fischer's medium, Neurobasal medium, and a mixed medium thereof. From these basal media, media to be used in the respective steps of the producing method according to the present invention may be prepared.

A medium to be used as a "medium containing an undifferentiated state-maintaining factor" (medium for maintaining undifferentiated state) according to the present invention is feeder-free and serum-free, and it may be prepared by adding an undifferentiated state-maintaining factor, a serum replacement described later, and an appropriate nutrient source, etc., to a basal medium. Specifically, for example, it may be prepared by adding bFGF, KSR, a non-essential amino acid (NEAA), L-glutamine, and 2-mercaptoethanol to a DMEM/F12 medium.

Also, a feeder-free medium containing an undifferentiated state-maintaining factor described later, which is on the market as a medium suitable for maintaining undifferentiated state, may be used as a medium for maintaining undifferentiated state.

A "serum-free medium" in the present invention means a medium which does not contain non-conditioned or unpurified serum. A medium which is mixed with a purified blood-derived or animal tissue-derived component (e.g., growth factor) is included in a serum-free medium according to the present invention, unless non-conditioned or unpurified serum is contained.

A serum-free medium may contain a serum replacement. Examples of a serum replacement include those containing appropriately albumin, transferrin, a fatty acid, a collagen precursor, a trace element, 2-mercaptoethanol, 3'-thiolglycerol, or an equivalent thereof. Such a serum replacement may be prepared by the method according to WO 98/30679. A commercially available product may be used as a serum replacement. Examples of such a commercial product include Knockout Serum Replacement (produced by Life Technologies, now ThermoFisher Scientific Inc.; hereinafter occasionally also referred to as KSR), Chemically Defined Lipid Concentrate (produced by Life Technologies), GlutaMAX (produced by Life Technologies), B-27 (produced by Life Technologies), N-2 Supplement (produced by Life Technologies), and ITS Supplement (produced by Life Technologies).

A serum-free medium may contain if needed a fatty acid or a lipid, an amino acid (e.g. a non-essential amino acid), a vitamin, a growth factor, a cytokine, an antioxidant, 2-mercaptoethanol, pyruvic acid, a buffer, an inorganic salt, etc.

In order to avoid complication of preparation, as a serum-free medium, a serum-free medium, to which an appropriate amount (for example, about 0.5% to about 30%, preferably about 1% to about 20%) of commercially available KSR (produced by Life Technologies) is added, may be used (for example, a medium obtained by adding about 8% of KSR and Chemically Defined Lipid Concentrate to a GMEM medium), or a serum-free medium obtained by adding an appropriate amount (for example, about 0.1 to 5%) of commercially available B27 (produced by Life Technologies) to a Neurobasal medium may be also used. As a KSR equivalent, for example, a medium disclosed in Japanese Translation of PCT International Application Publication No. 2001-508302 may be used.

A culture is preferably carried out in a serum-free medium. It is preferably carried out in such a serum-free medium, as a serum-free medium containing KSR or B27, or a medium under xeno-free conditions. In this regard, "xeno-free" means a condition in which components derived from an organism species different from the organism species of the cell to be cultured are eliminated.

In the present invention, a feeder cell is a cell other than stem cells, which is added to coexist when the stem cells are cultured. Examples of a feeder cell include murine fibroblasts (MEF, etc.), human fibroblasts, SNL cells, and STO cells. The feeder cell may be a feeder cell having received a growth suppression treatment. In this regard, examples of the growth suppressing treatment include a treatment with a growth inhibitor (for example, mitomycin C), or a treatment with gamma ray irradiation, or UV irradiation. However, according to the present invention, a culture is carried out preferably in the absence of a feeder cell (feeder-free condition).

In the present invention, absence of a feeder cell (feeder-free condition) means cultivation in the absence of a feeder cell. Examples of the absence of feeder cell include the condition that a feeder cell is not added as described above, and a condition that a feeder cell is substantially not contained (for example, the percentage of the feeder cell number with respect to the total cell number is 3% or less, and preferably 0.5% or less).

As a feeder-free medium usable as a medium for maintaining undifferentiated state, a large number of synthetic media have been developed and marketed, and there is, for example, Essential 8 (produced by Life Technologies). The Essential 8 medium contains as additives L-ascorbic acid-2-phosphate, magnesium (64 mg/L), sodium selenium (141.1 g/L), insulin (19.4 mg/L), NaHCO$_3$ (543 mg/L), transferrin (10.7 mg/L), bFGF (100 ng/mL), and a TGFβ1 agonist (TGF131 (2 ng/mL), or Nodal (100 ng/mL)) in a DMEM/F12 medium (Nature Methods, 8, 424-429 (2011)). Examples of a commercially available feeder-free medium containing an undifferentiated state-maintaining factor, namely a feeder-free medium usable as a medium for maintaining undifferentiated state include S-Medium (produced by DS Pharma Biomedical Co., Ltd.), StemPro (produced by Life Technologies), hESF9 (Proc Natl Acad Sci USA, 2008 Sep. 9: 105 (36): 13409-14), mTeSR 1 (produced by STEMCELL Technologies), mTeSR 2 (produced by STEMCELL Technologies), TeSR-E8 (produced by STEMCELL Technologies), and StemFit (produced by Ajinomoto Healthy Supply Co., Inc.). The present invention may be easily implemented by using any of these in Step (1).

<Extracellular Matrix>

In the present invention, the extracellular matrix is a supramolecular structure present outside the cell, and may be either a naturally-occurring substance or an artificial (recombinant) substance. Examples of the extracellular matrix include substances such as collagen, proteoglycan, fibronectin, hyaluronic acid, tenascin, entactin, elastin, fibrillin, and laminin, and fragments thereof. Two or more of these extracellular matrices may be used in combination. For example, the extracellular matrix may be a product prepared from cells, such as BD Matrigel (trademark). The extracellular matrix is preferably laminin or a fragment thereof. The laminin in the present invention is a protein having a heterotrimeric structure having one each of α chain, β chain, and γ chain, and is an extracellular matrix protein in which isoforms having different subunit chain compositions exist. Laminin has approximately 15 kinds of isoforms as combinations of heterotrimers of 5 kinds of α chains, 4 kinds of β chains, and 3 kinds of γ chains. For example, but not limited to, the α chain is α1, α2, α3, α4, or α5, the β chain is β1, β2, β3, or β4, and the γ chain is γ1, γ2, or γ3. Laminin to be used in the present invention is more preferably laminin-511 composed of α5, β1 and γ1 (Nat Biotechnol 28, 611-615 (2010)).

According to the present invention, laminin may be a fragment, and any fragment having integrin binding activity may be used without particular restriction. Laminin may be, for example, E8 fragment obtained by digestion with an elastase (EMBO J., 3: 1463-1468, 1984; or J. Cell Biol., 105: 589-598, 1987). Therefore, according to the present invention, a preferable example is laminin-511 E8 described in WO 2011/043405 (preferably human laminin-511 E8) obtained by digestion of laminin-511 with an elastase. In this regard, a laminin E8 fragment to be used in the present invention, such as laminin-511 E8 may not be a laminin digestion product by an elastase, and may be a recombinant. Laminin-511 E8 is on the market, and is commercially available, for example, from Nippi, Inc.

The laminin or laminin fragment to be used in the present invention is preferably isolated, from the viewpoint of avoiding contamination with unidentified components.

<Differentiation-Inducing Factor>

There is no particular restriction on a differentiation-inducing factor, insofar as it is a substance which induces differentiation of pluripotent stem cells to Corin positive and/or Lrtm1-positive cells, or dopaminergic neuron progenitor cells. Specific examples thereof include, BMP inhibitor, TGFβ inhibitor, SHH signal stimulant, FGF8 and GSK3β inhibitor.

<BMP Inhibitor>

In the present invention, there is no particular restriction on a BMP inhibitor, insofar as it is a substance to inhibit signal transduction caused by BMP, and it may be any of a nucleic acid, a protein, and a low molecular weight organic compound. Examples of BMP include BMP2, BMP4, BMP7, and GDF7. Examples of a BMP inhibitor may include a substance that acts directly on BMP (such as antibody, and aptamer), a substance that inhibits the expression of a gene encoding BMP (such as antisense oligonucleotide, and siRNA), a substance that inhibits the binding of a BMP receptor (BMPR) and BMP, and a substance that inhibits physiological activity caused by signal transduction by a BMP receptor. As examples of a BMPR, there are ALK2 and ALK3. As a BMP signal transduction pathway inhibitor, compounds well known to those skilled in the art may be used, and examples thereof include a proteinaceous inhibitor, such as Chordin, Noggin, and Follistatin, Dorsomorphin (i.e. 6-[4-(2-piperidin-1-yl-ethoxy)phenyl]-3-pyridin-4-yl-pyrazolo[1,5-a]pyrimidine) and a derivative thereof (P. B. Yu et al., Circulation, 116: II-60 (2007); P. B. Yu et al., Nat. Chem. Biol., 4: 33-41 (2008); J. Hao, et al., PLoS ONE, 3 (8): e2904 (2008)), and LDN 193189 (i.e. 4-[6-(4-piperazin-1-yl)phenyl)pyrazolo[1,5-a]pyrimidin-3-yl)quinoline). Here, LDN 193189 is well known as a BMPR (ALK2/3) inhibitor (hereinafter BMPR inhibitor), and is commercially available, for example in the form of a hydrochloride salt. Dorsomorphin and LDN 193189 are available from Sigma-Aldrich Co. and Stemgent, Inc., respectively. As a BMP inhibitor, one or more of these may be appropriately selected and used. A BMP inhibitor to be used in the present invention may be preferably LDN 193189.

Although there is no particular restriction on the concentration of LDN 193189 in a medium insofar as it is a concentration that inhibits BMP, it is for example, but not limited to, 1 nM, 10 nM, 50 nM, 100 nM, 500 nM, 750 nM, 1 µM, 2 µM, 3 µM, 4 µM, 5 µM, 6 µM, 7 µM, 8 µM, 9 µM, 10 µM, 15 µM, 20 µM, 25 µM, 30 µM, 40 µM, or 50 µM. Preferably, it is 100 nM.

<TGFβ Inhibitor>

In the present invention, a TGFβ inhibitor is a substance that inhibits signal transduction continuing from binding of TGFβ with a TGFβ receptor to SMAD, and there is no particular restriction insofar as it is a substance that inhibits the attributable signal transduction pathway, and it may be any of nucleic acid, protein, and low molecular weight organic compound. Examples of such substances include a substance that acts directly on TGFβ (such as a protein, an antibody, and an aptamer), a substance that inhibits expression of the gene encoding TGFβ (such as antisense oligonucleotide, and siRNA), a substance that inhibits binding of a TGFβ receptor with TGFβ, and a substance that inhibits the bioactivity caused by signal transduction by a TGFβ receptor (such as an inhibitor of TGF receptor, and a SMAD inhibitor). The examples further include a substance that inhibits the binding to the ALK family receptors, and a substance that inhibits phosphorylation of SMAD by the ALK family, such as Lefty-1 (for example, NCBI Accession No. NM-010094 for mouse; and No. NM_020997 for human), Lefty-2 (for example, NCBI Accession No. NM_177099 for mouse; and Nos. NM_003240 and NM_001172425 for human), SB 431542, SB202190 (all of the above are according to R. K. Lindemann, et al., Mol. Cancer, 2003, 2: 20), SB 505124 (GlaxoSmithKline), NPC 30345, SD 093, SD 908, SD 208 (Scios), LY 2109761, LY 364947, LY 580276 (Lilly Research Laboratories), A83-01 (WO 2009/146408), and derivatives thereof. Examples of a preferable TGFβ inhibitor to be used in the present invention include SB 431542 (4-(5-benzo[1,3]dioxol-5-yl-4-pyridin-2-yl-1H-imidazol-2-yl)benzamide), and A-83-01 (3-(6-methyl-2-pyridinyl)-N-phenyl-4-(4-quinolinyl)-1H-pyrazole-1-carbothioamide), and these are publicly known as an inhibitor of a TGF receptor (ALK 5), and an activin receptor (ALK4/7). As a TGFβ inhibitor, one, or more of these may be appropriately selected and used. The TGFβ inhibitor to be used in the present invention may be more preferably A83-01.

There is no particular restriction on the concentration of A83-01 in a medium insofar as it is a concentration that inhibits ALK5. For example, but not limited to, it is 1 nM, 10 nM, 50 nM, 100 nM, 500 nM, 750 nM, 1 µM, 2 µM, 3 µM, 4 µM, 5 µM, 6 µM, 7 µM, 8 µM, 9 µM, 10 µM, 15 µM, 20 µM, 25 µM, 30 µM, 40 µM, or 50 µM. It is preferably from 500 nM to 5 µM, and more preferably 500 nM.

In this regard, the TGFβ inhibitory activity of SB 431542, LDN 193189, etc. may be determined by a method well known to those skilled in the art, for example, by a method in which phosphorylation of Smad is detected by western blotting (Mol Cancer Ther. (2004) 3, 737-45).

The activity of an SHH stimulant, such as Purmorphamine, and SAG; may be determined by a method well known to those skilled in the art, for example, by a reporter gene assay focusing on expression of the Gli1 gene (Oncogene (2007) 26, 5163-5168)

<GSK3β Inhibitor>

In the present invention, the GSK3β inhibitor is defined as a substance which inhibits kinase activity (for example, capacity to phosphorylate β-catenin) of GSK-3β protein. A number of GSK3β inhibitors are known, and examples of the GSK3β inhibitors include BIO (another name, GSK-3β inhibitor IX; 6-bromoindirubin-3'-oxime), which is an indirubin derivative; SB216763 (3-(2,4-dichlorophenyl)-4-(1-methyl-1H-indol-3-yl)-1H-pyrrole-2,5-dione), which is a maleimide derivative; GSK-313 inhibitor VII (4-dibromoacetophenone), which is a phenyl α-bromomethyl ketone compound; L803-mts (another name, GSK-313 peptide inhibitor; Myr-N-GKEAPPAPPQpSP-NH$_2$ (SEQ ID NO:1)), which is a cell membrane-permeable phosphorylated peptide; and CHIR99021 (6-[2-[4-(2,4-dichlorophenyl)-5-(4-methyl-1H-imidazol-2-yl)pyrimidin-2-ylamino] ethyl amino]pyridine-3-carbonitrile), which has high selectivity. As the GSK3β inhibitor, one or more kinds of these may be appropriately selected and used. These compounds are commercially available from, for example, Calbiochem and Biomol, and can be easily employed. The compounds may also be obtained from other sources, or may be prepared. The GSK3β inhibitor to be used in the present invention may be preferably CHIR99021.

Examples of the concentration of CHIR99021 in the medium include, but are not limited to, 1 nM, 10 nM, 50 nM, 100 nM, 500 nM, 750 nM, 1 µM, 2 µM, 3 µM, 4 µM, 5 µM, 6 µM, 7 µM, 8 µM, 9 µM, 10 µM, 15 µM, 20 µM, 25 µM, 30 µM, 40 µM, and 50 µM. The concentration is preferably 1 µM.

<FGF8>

In the present invention, the FGF8 is not particularly limited, and, in cases of human FGF8, examples of the FGF8 include the following four splicing forms: FGF8a, FGF8b, FGF8e, and FGF8f, and FGF8b is more preferable. FGF8 is commercially available from, for example, Wako Pure Chemical Industries, Ltd. and R&D Systems, Inc., and can be easily employed. The FGF8 may also be obtained by forced expression in cells by a method known to those skilled in the art.

Examples of the concentration of FGF8 in the medium include, but are not limited to, 1 ng/mL, 5 ng/mL, 10 ng/mL, 50 ng/mL, 100 ng/mL, 150 ng/mL, 200 ng/mL, 250 ng/mL, 500 ng/mL, 1000 ng/mL, 2000 ng/mL, and 5000 ng/mL. The concentration is preferably 100 ng/mL.

<Corin-Positive Cells and/or Lrtm1-Positive Cells>

Corin-positive cells and/or Lrtm1-positive cells are cells in which a Corin protein and/or an Lrtm1 protein has been expressed in an amount recognizable by an anti-Corin antibody or an anti-Lrtm1 antibody. In other words, an example is cells in which a Corin protein, or an Lrtm1 protein has expressed on the cell surface in an amount recognizable by the following "Method for Selecting Cells".

<Method for Selecting Cells>

In the present invention, the selection of Corin-positive cells and/or Lrtm1-positive cells from a cell population may be carried out using a substance(s) that specifically bind(s) to Corin and/or Lrtm1. As a substance that binds to Corin or Lrtm1, an antibody or an aptamer may be used. The substance is preferably an antibody or an antigen-binding fragment thereof.

In the present invention, the antibody may be either a polyclonal or monoclonal antibody. These antibodies can be prepared using techniques well known to those skilled in the art (Current protocols in Molecular Biology, edit. Ausubel et al. (1987) Publish. John Wiley and Sons., Sections 11.12-11.13). More specifically, in cases where the antibody is a polyclonal antibody, the polyclonal antibody can be obtained by allowing E. coli, a mammalian cell line, or the like to express a protein encoded by Corin or Lrtm1, or an oligopeptide or a glycolipid having a partial amino acid sequence thereof, according to a conventional method, and purifying the resulting expression product, followed by immunization of a non-human mammal such as a rabbit therewith, and isolating the polyclonal antibody from the serum of the immunized animal according to a conventional method. In cases where the antibody is a monoclonal antibody, the monoclonal antibody can be obtained from hybridoma cells prepared by cell fusion of spleen cells obtained from the above-described immunized non-human mammal with myeloma cells (Current protocols in Molecular Biology, edit. Ausubel et al. (1987) Publish. John Wiley and Sons., Section 11.4-11.11). Examples of the antigen-binding fragment of the antibody include parts of the antibody (e.g., Fab fragment) and synthetic antibody fragments (e.g., single-chain Fv fragment "ScFv"). Antibody fragments such as the Fab and F(ab)$_2$ fragments can also be prepared by well-known methods in genetic engineering. For example, an antibody against Corin can be obtained by the preparation methods described in WO 2004/065599 and WO 2006/009241, and an antibody against Lrtm1 can be obtained by the preparation method described in WO 2013/015457.

A sequence of human Corin can be obtained from NCBI accession No. NM_006587. Similarly, a sequence of human Lrtm1 can be obtained from NM_020678.

For the purpose of recognition or separation of cells expressing Corin or Lrtm1, the binding substance may be bound or conjugated, for example, to a detectable substance, such as a fluorescent label, radioactive label, chemiluminescent label, enzyme, biotin, or streptavidin, or to a substance that allows isolation/extraction of the cells, such as protein A, protein G, beads, or magnetic beads.

Alternatively, the binding substance may be indirectly labeled. The labeling may be carried out by various methods known to those skilled in the art, and examples of the methods include a method in which a preliminarily labeled antibody (secondary antibody) that specifically binds to the antibody is used.

Examples of the method for detecting the dopaminergic neuron progenitor cells include use of a flow cytometer, protein chip, or the like.

Examples of the method for extracting the dopaminergic neuron progenitor cells include a method in which the binding substance is conjugated to particles to cause precipitation of the resulting conjugate, a method in which the cells are sorted by magnetism using magnetic beads (e.g., MACS), a method in which a fluorescent label and a cell sorter are used, and a method in which a carrier (e.g., cell-concentrating column) to which an antibody or the like is immobilized is used.

In the present invention, the aptamer which specifically binds to Corin or Lrtm1 can be prepared using a technique well known to those skilled in the art (SELEX (systematic evolution of ligand by exponential enrichment) method: Ellington, A. D. & Szostak, J. W. (1990) Nature, 346, 818-822; Tuerk, C. & Gold, L. (1990) Science, 249, 505-510).

<Neurotrophic Factor>

In the present invention, the neurotrophic factor means a ligand for a membrane receptor playing an important role in survival and maintenance of the function of motor neurons. Examples of the neurotrophic factor include Nerve Growth Factor (NGF), Brain-derived Neurotrophic Factor (BDNF), Neurotrophin 3 (NT-3), Neurotrophin 4/5 (NT-4/5), Neurotrophin 6 (NT-6), basic FGF, acidic FGF, FGF-5, Epidermal Growth Factor (EGF), Hepatocyte Growth Factor (HGF), Insulin, Insulin Like Growth Factor 1 (IGF 1), Insulin Like Growth Factor 2 (IGF 2), Glia cell line-derived Neurotrophic Factor (GDNF), TGF-β2, TGF-β3, Interleukin 6 (IL-6), Ciliary Neurotrophic Factor (CNTF), and LIE One or more of these may be appropriately selected and used. In the present invention, the neurotrophic factor is preferably a factor selected from the group consisting of GDNF and BDNF. Neurotrophic factors are commercially available from, for example, Wako Pure Chemical Industries, Ltd. and R&D Systems, Inc., and can be easily employed. The neurotrophic factor may also be obtained by forced expression in cells by a method known to those skilled in the art.

Examples of the concentration of GDNF1 in the medium include, but are not limited to, 0.1 ng/mL, 0.5 ng/mL, 1 ng/mL, 5 ng/mL, 10 ng/mL, 15 ng/mL, 20 ng/mL, 25 ng/mL, 30 ng/mL, 40 ng/mL, 50 ng/mL, 100 ng/mL, 200 ng/mL, and 500 ng/mL. The concentration is preferably 10 ng/mL. Examples of the concentration of BDNF1 in the medium include, but are not limited to, 0.1 ng/mL, 0.5 ng/mL, 1 ng/mL, 5 ng/mL, 10 ng/mL, 15 ng/mL, 20 ng/mL, 25 ng/mL, 30 ng/mL, 40 ng/mL, 50 ng/mL, 100 ng/mL, 200 ng/mL, and 500 ng/mL. The concentration is preferably 20 ng/mL.

<ROCK Inhibitor>

In the present invention, there is no particular restriction on the ROCK inhibitor, insofar as it can suppress the function of Rho kinase (ROCK), and examples thereof include Y-27632 (for example, refer to Ishizaki et al., Mol. Pharmacol. 57, 976-983 (2000); and Narumiya, et al., Methods Enzymol. 325, 273-284 (2000)), Fasudil/HA1077 (for example, refer to Uenata et al., Nature 389: 990-994 (1997)), H-1152 (for example, refer to Sasaki et al., Pharmacol. Ther. 93: 225-232 (2002)), Wf-536 (for example, refer to Nakajima et al., Cancer Chemother Pharmacol. 52 (4): 319-324 (2003)), and derivatives thereof, as well as antisense nucleic acids to ROCK, RNA interference inducing nucleic acids (e.g. siRNA), dominant negative mutants, and their expression vectors. Since other low molecular weight compounds are also known as ROCK inhibitors, such compounds or derivatives thereof may also be used in the present invention (for example, refer to U.S. Unexamined Patent Application Publication No. 20050209261, No. 20050192304, No. 20040014755, No. 20040002508, No. 20040002507, No. 20030125344, and No. 20030087919, and International Publication No. WO 2003/062227, No. WO 2003/059913, No. WO 2003/062225, No. WO 2002/076976, and No. WO 2004/039796). In the present invention, one or more ROCK inhibitors may be used. The ROCK inhibitor to be used in the present invention may preferably be Y-27632.

The concentration of Y-27632 is, for example, but not limited to, 100 nM, 500 nM, 750 nM, 1 μM, 2 μM, 3 μM, 4 μM, 5 μM, 6 μM, 7 μM, 8 μM, 9 μM, 10 μM, 15 μM, 20 μM, 25 μM, 30 μM, 40 μM, or 50 μM. It is preferably 10 μM.

A "medium containing a substance X" and "in the presence of a substance X" mean herein a medium to which an exogenous substance X is added, or a medium which contains an exogenous substance X, and a medium in which an exogenous substance X is present. In other words, in a case where a cell or a tissue existing in the medium expresses, secretes or produces the substance X endogenously, the endogenous substance X is distinguished from an exogenous substance X, and a medium which does not contain an exogenous substance X is deemed outside the category of a "medium containing a substance X", even when it contains an endogenous substance X.

II. Method for Producing Cell Population Containing Corin Positive and/or Lrtm1-Positive Cells The present invention provides a method for producing a cell population containing Corin positive and/or Lrtm1-positive cells, comprising the following steps (1) and (2):

(1) a step of performing adhesion culture of pluripotent stem cells in a medium for maintaining undifferentiated state containing an SHE signal stimulant, and an undifferentiated state-maintaining factor in the absence of feeder cells, and
(2) a step of culturing the cell population obtained in Step (1) in a medium containing one or more differentiation-inducing factors.

<Step (1)>

As the pluripotent stem cell in Step (1), for example, an induced pluripotent stem cell and an embryonic stem cell (iPS cell and ES cell) are preferable, and a human induced pluripotent stem cell and a human embryonic stem cell (human iPS cell and human ES cell) are more preferable. There is no particular restriction on a method for producing induced pluripotent stem cells, and they may be produced by a method well known to those skilled in the art as described above. However, it is preferable that a step of producing induced pluripotent stem cells (i.e. a step of reprogramming somatic cells to establish pluripotent stem cells) is also carried out in a feeder-free condition. In this regard, there is no particular restriction on a method for obtaining embryonic stem cells (ES cells), and it may be produced by a method well known to those skilled in the art as described above, but the method for producing embryonic stem cells (ES cells) is also preferably carried out in a feeder-free condition.

The maintenance culture and expansion culture of pluripotent stem cells can be carried out in an adhesion culture, and also in a suspension culture, however preferably in an adhesion culture. The maintenance culture and expansion culture of pluripotent stem cells may be carried out in the presence of a feeder, or may be carried out in a feeder-free condition, however preferably in a feeder-free condition. Absence of a feeder cell (feeder-free condition) in the maintenance culture and expansion culture of pluripotent stem cells means a condition in which there exists substantially no feeder cell (for example, the percentage of the number of feeder cells with respect to the total cell number is 3% or less). The maintenance culture and expansion culture of pluripotent stem cells is preferably carried out in a feeder-free condition. The maintenance culture and expansion culture of pluripotent stem cells may be carried out in the presence of a ROCK inhibitor.

The maintenance culture and expansion culture of pluripotent stem cells in Step (1) may be carried out in a medium for maintaining undifferentiated state by a method well known to those skilled in the art.

There is no particular restriction on a medium for maintaining undifferentiated state to be used in Step (1), insofar as it is a medium, which is prepared by adding an undifferentiated state-maintaining factor to a basal medium, and in which pluripotent stem cells can survive while maintaining pluripotency. In this regard, the undifferentiated state-maintaining factor, and the basal medium are as described above. Specifically, a commercially available pluripotent stem cell medium, in which an undifferentiated state-maintaining factor has already been added, may be used as a medium for maintaining undifferentiated state used in Step (1), and the undifferentiated state-maintaining factor is preferably bFGF, TGFβ, or the like. Examples of the medium for maintaining undifferentiated state include Essential 8 (produced by Life Technologies), S-Medium (produced by DS Pharma Biomedical), StemPro (produced by Life Technologies), hESF9 (Proc Natl Acad Sci USA 2008 Sep. 9: 105 (36): 13409-14), mTeSR1 (produced by STEMCELL Technologies), mTeSR2 (produced by STEMCELL Technologies), TeSR-E8 (produced by STEMCELL Technologies), and StemFit (produced by Ajinomoto Healthy Supply Co., Inc.), and preferably Essential 8, and StemFit. The ROCK inhibitor described above may be appropriately added to the medium for maintaining undifferentiated state.

Absence of a feeder cell (feeder-free condition) in Step (1) means a condition in which there exists substantially no feeder cell (for example, the percentage of the number of feeder cells with respect to the total cell number is 3% or less). Preferably, Step (1) is performed under a feeder-free condition.

Culture of pluripotent stem cells in Step (1) may be performed under a condition of either suspension culture or adhesion culture, but is preferably carried out by an adhesion culture.

There is no particular restriction on a culture vessel to be used for carrying out the adhesion culture, insofar as an adhesion culture is possible, however a cell adhesive culture vessel is preferable. Examples of a cell adhesive culture vessel include a culture vessel which surface is artificially treated for improvement of adhesion with cells, and specific examples include a culture vessel which inside is covered with a coating agent. Examples of the coating agent include laminins [laminin α5β1γ1 (hereinafter referred to as laminin-511), laminin α1β1γ1 (hereinafter referred to as laminin-111), etc., and a laminin fragment (laminin-511 E8, etc.)], entactin, collagen, gelatin, vitronectin, Synthemax (Corning Incorporated), an extracellular matrix such as Matrigel, etc., and polymers such as polylysine and polyornithine. It is also possible to use a culture vessel having received a surface treatment such as a positive charge treatment. A preferable example is laminin, and laminin-511 E-8 is more preferable. Laminin-511 E-8 can be purchased from the market (e.g. iMatrix-511, Nippi, Inc.).

A medium to be used in Step (1) contains an SHH stimulant. In Step (1), Corin-expressing cells can be produced with high efficiency by first treating pluripotent stem cells with an SHH stimulant, and then subjecting the same to an adhesion culture in Step (2) in the presence of a differentiation-inducing factor.

The concentration of the SHH stimulant may be appropriately set within a range that allows achievement of the above-mentioned effect. For example, the Shh protein is usually used at a concentration of from 20 to 1000 ng/mL, and preferably from 50 to 300 ng/mL. SAG is usually used at a concentration of from 1 to 2000 nM, preferably from 10 to 700 nM, more preferably 30 to 600 nM, and further preferably from 30 to 300 nM. PMA is usually used at a concentration of from 0.002 to 20 μM, and preferably from 0.02 to 2 μM. Also, in one embodiment, the SHH stimulant may be appropriately used in an amount exhibiting an SHH stimulating effect equivalent to that of SAG at the above-mentioned concentration.

A medium to be used in Step (1) may be either a serum medium or a serum-free medium, however, from the viewpoint of avoiding contamination with a chemically unidentified component, it is preferably a serum-free medium.

A medium to be used in Step (1) may be a medium containing chemically identified components from the viewpoint of avoiding contamination with a chemically unidentified component.

In a culture of pluripotent stem cells under a feeder-free condition in Step (1), an appropriate matrix may be used as a scaffold in order to provide pluripotent stem cells with a scaffold substituting for feeder cells. Pluripotent stem cells are cultured by adhesion culture in a cell vessel which surface is coated with the matrix serving as a scaffold.

Examples of a matrix which is usable as a scaffold include laminin (Nat Biotechnol 28, 611-615 (2010)), a laminin fragment (Nat Commun 3, 1236 (2012)), a basement membrane preparation (Nat Biotechnol 19, 971-974 (2001)), gelatin, collagen, heparan sulfate proteoglycan, entactin, and vitronectin.

Preferably, in the culture of pluripotent stem cells under a feeder-free condition in Step (1), the pluripotent stem cells are cultured by performing adhesion culture in a cell vessel which surface is coated with isolated laminin-511, or a laminin-511 E8 fragment (more preferably laminin-511 E8 fragment).

There is no particular restriction on the culturing time of pluripotent stem cells in Step (1), insofar as the improvement effect of the quality of a cell population formed in Step (2) is achievable. It is usually from 0.5 to 48 hours. The culture time of pluripotent stem cells in Step (1) is preferably 1 hour or more, 2 hours or more, 6 hours or more, 12 hours or more, 18 hours or more, or 24 hours or more. The culture time of pluripotent stem cells in Step (1) is preferably 36 hours or less, or 28 hours or less. In an embodiment, the range of the culture time of pluripotent stem cells in Step (1) is preferably from 2 to 48 hours, more preferably from 6 to 48 hours, further preferably from 12 to 36 hours, and still further preferably from 18 to 28 hours (e.g. 24 hours). In other words, the first step is started from 0.5 to 48 hours (preferably from 18 to 28 hours) before the start of Step (2), and after completion of Step (1), Step (2) is subsequently performed. In another embodiment, the range of the culture time of pluripotent stem cells in Step (1) is preferably from 18 to 48 hours, from 18 to 36 hours, from 18 to 28 hours, or from 24 to 28 hours. When cells are treated with an SHH signal stimulant, and the cells are subsequently subjected to another treatment, each treatment time may be within the above-mentioned culture time. Usually, Step (1) is performed without adding a ROCK inhibitor.

The culture conditions, such as culture temperature, and $CO_2$ concentration in Step (1) may be selected appropriately. The culture temperature is, for example, from about 30° C. to about 40° C., and preferably about 37° C. Meanwhile, the $CO_2$ concentration is, for example, from about 1% to about 10%, and preferably about 5%.

In a preferable embodiment, human pluripotent stem cells (e.g. human iPS cells) are cultured by adhesion culture in a serum-free medium containing bFGF and an SHH signal stimulant in the absence of feeder cells. The adhesion culture is preferably carried out in a cell vessel which surface is coated with laminin-511, a laminin-511 E8 fragment, or vitronectin. The adhesion culture is preferably carried out using as a feeder-free medium, Essential 8, a TeSR medium, an mTeSR medium, an mTeSR-E8 medium, or a StemFit medium, and more preferably using Essential 8, or a StemFit medium.

In a preferable embodiment, human pluripotent stem cells (e.g. human iPS cells) are cultured by suspension culture in a serum-free medium containing bFGF and an SHE signal stimulant in the absence of feeder cells. In the suspension culture, the human pluripotent stem cells may form aggregates of human pluripotent stem cells.

In a preferable embodiment, the cells obtained in Step (1) are cells maintaining a pluripotent-like state, and the pluripotent-like state is maintained through Step (1). The pluripotent-like state means a state in which at least part of traits common among pluripotent stem cells including pluripotency are maintained. The pluripotent-like state does not require strict pluripotency. Specifically, "pluripotent-like state" includes a state in which all or part of markers to indicate a pluripotent state are expressed. Examples of the markers to indicate a pluripotent-like state include Oct3/4 positivity, and alkaline phosphatase positivity. In an embodiment, a cell maintaining pluripotent-like state is Oct3/4-positive. Even when the expression level of Nanog is lower than that of ES cells or iPS cells, it corresponds to a "cell in a pluripotent-like state".

In an embodiment, the cells obtained in Step (1) are stem cells capable of differentiating into Corin positive and/or Lrtm1 positive cells, dopaminergic neuron progenitor cells, or dopaminergic neural cells. In an embodiment, the cells obtained in Step (1) are Oct3/4 positive stem cells capable of differentiating into at least Corin positive and/or Lrtm1 positive cells, dopaminergic neuron progenitor cells, or dopaminergic neural cells.

In a preferable embodiment, human pluripotent stem cells (e.g. iPS cells) are cultured by adhesion culture in a serum-free medium containing an SHE signal stimulant and bFGF in the absence of feeder cells.

The adhesion culture is preferably carried out in a cell vessel which surface is coated with laminin-511 or a laminin-511 E8 fragment. The SHE signal stimulant is preferably an SHH protein, SAG or Purmorphamine (PMA), and more preferably SAG The SHH signal stimulant (e.g. Shh protein, SAG, or PMA) may be used in a combination with a TGFβ inhibitor (e.g. Lefty, SB 431542, A-83-01), or a BMP inhibitor (e.g. LDN 193189) may be used in combination. Specifically, for example, a combination of SAG and A-83-01, or SAG and LDN 193189 may be used. The incubation time is from 0.5 to 48 hours (preferably from 18 to 48 hours, from 18 to 36 hours, from 18 to 28 hours, or from 24 to 28 hours).

Step (1) is implemented, for example, such that first pluripotent stem cells are cultured and maintained in a medium containing an undifferentiated state-maintaining factor (medium for maintaining undifferentiated state) in the absence of feeder cells, then an SHH signal stimulant is added into the medium, or the medium is exchanged with a medium for maintaining undifferentiated state containing an SHH signal stimulant to continue the culture.

For example, human pluripotent stem cells (e.g. human iPS cells) are cultured and maintained in a serum-free medium containing bFGF in the absence of feeder cells. The maintenance culture is preferably carried by adhesion culture. The adhesion culture is preferably carried out in a cell vessel which surface is coated with vitronectin, laminin-511, or laminin-511 E8 fragments. Then, in Step (1), an SHH signal stimulant is added to the medium and the culture is continued. The SHH signal stimulant is preferably an SHH protein, SAG or PMA. In this regard, a TGFβ inhibitor (e.g. Lefty, SB 431542, or A-83-01), or a BMP inhibitor (e.g. LDN 193189) may be used in a combination with an SHE signal stimulant (e.g. Shh protein, SAG; or PMA) may be used in combination. After the addition, the culture is continued for 0.5 to 48 hours (preferably from 18 to 48 hours, from 18 to 28 hours, or about 24 hours).

<Step (2)>

According to the present invention, Step (2) may be implemented using a medium containing a differentiation-inducing factor capable of inducing differentiation of pluripotent stem cells to Corin positive and/or Lrtm1 positive cell, and it is preferable that the Step is performed by the following multistage steps of:

(a) performing adhesion culture of pluripotent stem cells on an extracellular matrix in a medium containing a BMP inhibitor, and a TGFβ inhibitor;

(b) performing adhesion culture of the cells obtained in Step (a) on an extracellular matrix in a medium containing a BMP inhibitor, TGFβ inhibitor, SHH signal-stimulant, and FGF8;

(c) performing adhesion culture of the cells obtained in Step (b) on an extracellular matrix in a medium containing a BMP inhibitor, TGFβ inhibitor, SHH signal stimulant, FGF8, and GSK3β inhibitor; and (d) performing adhesion culture of the cells obtained in Step (c) on an extracellular matrix in a medium containing a BMP inhibitor, and a GSK3β inhibitor.

In the present invention, the medium to be used in Step (2) may be prepared using a medium for animal cell culture, specifically a medium, well known to those skilled in the art, and used for cell differentiation of undifferentiated cells such as pluripotent stem cells, as a basal medium. Examples of the basal medium include Glasgow's Minimal Essential Medium (GMEM), IMDM, Medium 199, Eagle's Minimum Essential Medium (EMEM), αMEM, Dulbecco's modified Eagle's Medium (DMEM), Ham's F12 medium, RPMI 1640 medium, Fischer's medium, Neurobasal Medium (produced by Life Technologies), and mixtures of two or more of these media. The medium is preferably GMEM. The medium may contain serum, or may be serum-free. If necessary, the medium may contain one or more of serum replacements, such as albumin, transferrin, Knockout Serum Replacement (KSR) (serum replacement), N2 supplement (Invitrogen), B27 Supplement (Invitrogen), fatty acids, insulin, collagen precursor, trace elements, 2-mercaptoethanol, and 3'-thioglycerol, and may also contain one or more of substances, such as lipids, amino acids, L-glutamine, GlutaMax (produced by Life Technologies), non-essential amino acids, vitamins, growth factors, low-molecular-weight compounds, antibiotics, antioxidants, pyruvic acid, buffers, and inorganic salts. A preferable medium is a GMEM medium, which contains KSR, 2-mercaptoethanol, non-essential amino acids, and pyruvic acid.

The culture may be carried out after appropriately supplementing the medium with a reagent(s) selected from the group consisting of the BMP inhibitor, the TGFβ inhibitor, the SHH signal stimulants, the FGF8, and the GSK3β inhibitors, for the sake of differentiation to a cell population containing Corin positive and/or Lrtm1 positive cells.

As the SHH signal stimulant to be used in Step (2), and in a case where Step (2) is carried out by Steps (a), (b), (c) and (d), to be used in Step (b) and Step (c) of Step (2), any one, or two or more kinds of SHH signal stimulants described above may be appropriately selected and used, and preferably Purmorphamine is used.

There is no particular restriction on the concentration of Purmorphamine in the medium, insofar as it is a concentration adequate for activating Gli 2. It may be, for example, but without limitation to, 1 nM, 10 nM, 50 nM, 100 nM, 500 nM, 750 nM, 1 µM, 2 µM, 3 µM, 4 µM, 5 µM, 6 µM, 7 µM, 8 µM, 9 µM, 10 µM, 15 µM, 20 µM, 25 µM, 30 µM, 40 µM, 50 µM, and preferably 2 µM.

An adhesion culture in the presence of an extracellular matrix, preferably on the extracellular matrix in Step (2) may be carried out by culturing the cells using a culture vessel coated with an extracellular matrix. The coating treatment may be carried out by placing a solution containing the extracellular matrix in the culture vessel, and then removing the solution as appropriate.

Usually, Step (a) of Step (2) is performed in a medium further containing a ROCK inhibitor. In other words, Step (a) may be a step of performing adhesion culture of pluripotent stem cells in a medium containing a ROCK inhibitor, a BMP inhibitor, and a TGFβ inhibitor on an extracellular matrix.

In terms of the culture conditions, the culture temperature is not limited, and may be about 30 to 40° C., preferably about 37° C. The culture is carried out in an atmosphere of $CO_2$-containing air, wherein the $CO_2$ concentration is preferably about 2 to 5%.

Although the culture period is not particularly limited as long as Corin positive and/or Lrtm1 positive cells appear during the period, it is preferable to carry out the culture such that the percentage of Corin positive and/or Lrtm1 positive cells in the cell population obtained after the end of Step (2) becomes 10% or more, and to continue Step (2) for at least 10 days. The period of Step (2) is more preferably 12 days to 21 days, and still more preferably 12 days to 14 days.

In Step (2), examples of the period of Step (a) include not less than 1 day, not less than 2 days, not less than 3 days, not less than 4 days, not less than 5 days, not less than 6 days, not less than 7 days, and periods longer than these. The period of Step (a) is preferably 1 day. Similarly, examples of the period of Step (b) include not less than 1 day, not less than 2 days, not less than 3 days, not less than 4 days, not less than 5 days, not less than 6 days, not less than 7 days, and periods longer than these. The period of Step (b) is preferably 2 days. Similarly, examples of the period of Step (c) include not less than 1 day, not less than 2 days, not less than 3 days, not less than 4 days, not less than 5 days, not less than 6 days, not less than 7 days, and periods longer than these. The period of Step (c) is preferably 4 days. Similarly, examples of the period of Step (d) include not less than 1 day, not less than 2 days, not less than 3 days, not less than 4 days, not less than 5 days, not less than 6 days, not less than 7 days, and periods longer than these. The period of Step (d) is preferably 5 days.

The pluripotent stem cells may be dissociated. Examples of the method for dissociating the pluripotent stem cells include a method in which the cells are mechanically dissociated, and a method in which a dissociation solution having protease activity and collagenase activity (e.g., Accutase (trademark) or Accumax (trademark)), or a dissociation solution having only collagenase activity is used. Preferably a method in which human pluripotent stem cells are dissociated using trypsin or a replacement thereof (e.g., TrypLE CTS (Life Technologies)) is used. In cases where the cells are dissociated, it is preferable to add a ROCK inhibitor as appropriate after the dissociation, followed by performing culture of the dissociated cells. In cases where a ROCK inhibitor is added, the culture in the presence of the ROCK inhibitor may be carried out for at least one day. The culture is more preferably carried out for one day.

III. Method for Producing Dopaminergic Neuron Progenitor Cells

<Step (3)>

A step of collecting Corin positive and/or Lrtm1 positive cells of Step (3) may be carried out based on the aforedescribed <Method for Selecting Cells>.

<Step (4)>

The medium to be used in Step (4) may be prepared using a medium for animal cell culture as a basal medium. Examples of the basal medium include Glasgow's Minimal Essential Medium(GMEM), IMDM, Medium 199, Eagle's Minimum Essential Medium (EMEM), αMEM, Dulbecco's modified Eagle's Medium (DMEM), Ham's F12 medium, RPMI 1640 medium, Fischer's medium, Neurobasal Medium (produced by Life Technologies), and mixtures of two or more of these media. The medium is preferably Neurobasal Medium. The medium may contain serum, or may be serum-free. If necessary, the medium may contain one or more of serum replacements such as albumin, transferrin, Knockout Serum Replacement (KSR) (serum replacement for FBS in ES cell culture), N2 supplement (Invitrogen), B27 Supplement (Invitrogen), fatty acids, insulin, collagen precursor, trace elements, 2-mercaptoethanol, and 3'-thiolglycerol, and may also contain one or more of substances, such as lipids, amino acids, L-glutamine, GlutaMax (produced by Life Technologies), non-essential amino acids, vitamins, growth factors, low-molecular-weight compounds, antibiotics, antioxidants, pyruvic acid, buffers, inorganic salts, and nucleic acids (for example, dibutyryl cyclic AMP (dbcAMP)). A preferable medium is Neurobasal Medium supplemented with B27 Supplement, ascorbic acid, and dbcAMP. By adding a neurotrophic factor(s) to the medium, culture can be performed.

The suspension culture in Step (4) means culturing of the cells in a state where the cells are not adhering to the culture vessel. The culture vessel that may be used is not limited, and examples of the culture vessel include culture vessels that are not artificially treated for the purpose of enhancing adhesiveness to cells (for example, by coating treatment with an extracellular matrix or the like), and culture vessels that are artificially treated such that adhesion is suppressed (for example, by coating treatment with a polyhydroxyethylmethacrylate (poly-HEMA), a nonionic surface-active polyol (e.g., Pluronic F-127), or a phospholipid analogue (e.g., a water-soluble polymer containing 2-methacryloyloxyethyl phosphorylcholine as a constituent (Lipidure)).

In terms of the culture conditions, the culture temperature is not limited, and may be about 30 to 40° C., preferably about 37° C. The culture is carried out in an atmosphere of $CO_2$-containing air, wherein the $CO_2$ concentration is preferably about 2 to 5%.

The culture period is not limited as long as NuiT1 positive and/or Foxa2 positive cells appear during the period. Step (4) is preferably carried out for at least 7 days. The period is more preferably 7 days to 30 days, still more preferably 14 days to 21 days, or 14 days to 16 days. The period is most preferably 16 days.

In cases where Step (4) is carried out after Step (3), it is preferable to add a ROCK inhibitor as appropriate to carry out the culture. In cases where a ROCK inhibitor is added, the culture in the presence of the ROCK inhibitor may be carried out for at least one day. The culture is more preferably carried out for one day.

IV. Pharmaceuticals

<Therapeutic Agent for Parkinson's Disease>

The dopaminergic neuron progenitor cells obtained by the present invention may be prepared as a formulation for administration to patients with Parkinson's disease. The administration is carried out by suspending the obtained dopaminergic neuron progenitor cells in physiological saline or the like, and transplanting the resulting suspension to the striatal region of the patient. Accordingly, the present invention provides a therapeutic agent for Parkinson's disease comprising dopaminergic neuron progenitor cells obtained from pluripotent stem cells by the above-described method.

In the present invention, the number of dopaminergic neuron progenitor cells contained in the therapeutic agent for Parkinson's disease is not limited as long as the transplant can engraft after the administration. For example, not less than $15 \times 10^4$ cells may be contained. The number of the cells may be increased or decreased as appropriate depending on symptoms and/or the size of the body.

The transplantation of the dopaminergic neuron progenitor cells to the affected area may be carried out by a method described in, for example, Nature Neuroscience, 2, 1137 (1999) or N Engl J Med. 344: 710-9 (2001).

<Kit>

Other embodiments of the present invention include a kit for preparation of dopaminergic neuron progenitor cells from pluripotent stem cells. The kit comprises a medium, additive, culture vessel, and/or the like to be used for the above-described steps of preparation of dopaminergic neuron progenitor cells. For example, the kit may contain an anti-Corin antibody and/or an anti-Lrtm1 antibody, an SHH signal stimulant (e.g. SAG) used in Step (1), a BMP inhibitor (e.g. LDN 193189), a TGFβ inhibitor (e.g. A83-01), an SHH signal stimulant (e.g. Purmorphamine), FGF8, a GSK3β inhibitor (e.g. CHIR 99021), an extracellular matrix (e.g. laminin-511 E8), and neurotrophic factor (e.g. BDNF and GDNF), used in Step (2). The kit may further contain a document or an instruction in which a procedure for the production process is described.

The present invention is described below more concretely by way of Examples. However, needless to say, the present invention is not limited to these.

Example 1

Cells and Culture

A protocol for production of dopamine producing cells is shown in FIG. 1.

QHJ-I 01, which is a human iPS cell, has been produced by introducing of Oct3/4, Sox2, Klf4, L-MYC, LIN28, and a dominant-negative form of p53 (Okita, K., et al., Stem Cells, 31, 458-66 (2013); WO2013/176233) into human PBMC by an episomal vector. The cells were received from Professor Yamanaka of Kyoto University, et al.

The iPS cells were cultured according to the method described by Miyazaki T, et al., Nat Commun. 3: 1236, 2012. Specifically, maintenance culture was performed in a medium for maintaining undifferentiated state containing FGF2 (bFGF) on a 6-well plate coated with Laminin-511 E8.

24 hours before the start of differentiation induction by exchange with a differentiation medium, the medium was exchanged with StemFit AK03N (Ajinomoto Healthy Supply Co., Inc.), which was a medium for maintaining undifferentiated state containing SAG (Enzo Life Sciences, Inc., 300 nM), an SHH signal stimulant, to obtain a cell population comprising iPS cells.

The cell population comprising iPS cells after culturing for 24 hours in the presence of SAG as described above was dissociated using TrypLE CTS (Life Technologies), and the cells were inoculated on a 6-well plate coated with Laminin-511 E8 (iMatrix-511 Nippi, Inc.) prepared separately, in an amount of $5 \times 10^6$ cells per well. The medium was replaced with a differentiation medium [a basal medium A [GMEM (Invitrogen) supplemented with 8% KSR (Invitrogen), 1 mM Sodium pyruvate (Invitrogen), 0.1 mM MEM nonessential amino acid (Invitrogen), and 0.1 mM 2-Mercaptoethanol (WAKO)] containing 10 μM Y-27632 (WAKO), 0.1 μM LDN 193189 (Stemgent, Inc.), and 0.5 μM A83-01 (WAKO)]. On the next day (Day 1), the medium was replaced with Basal Medium A supplemented with 0.1 μM LDN193189, 0.5 μM A83-01, 2 μM Purmorphamine (WAKO), and 100 ng/mL FGF8 (WAKO). Two days later (Day 3), the medium was replaced with Basal Medium A supplemented with 0.1 μM LDN193189, 0.5 μM A83-01, 2 μM Purmorphamine, 100 ng/mL FGF8, and 3 μM CHIR99021 (WAKO). Four days later (Day 7), the medium was replaced with Basal Medium A supplemented with 0.1 μM LDN193189 and 3 μM CHIR99021. During the above period, the medium was replaced once a day. A flow cytometry analysis using an anti-Corin antibody was performed on the 12th day of the start of differentiation induction (Day 12) (FIG. 1).

An anti-Corin antibody was prepared by the following method. First, from the Corin gene of *Macaca fascicularis*, a gene sequence encoding a part of the extracellular domain (79th-453rd amino acids) was introduced into 293E cells, and the cells were then allowed to express the extracellular-domain fragment of Corin protein, followed by collecting the protein. Mice were immunized with the recovered protein, and lymphocytes were then extracted and fused with myeloma cells. From the cell population after the fusion, a clone having reactivity with Corin was selected. The culture supernatant of the clone was used after attaching a fluorescent label as the anti-Corin monoclonal antibody.

Figure 2:
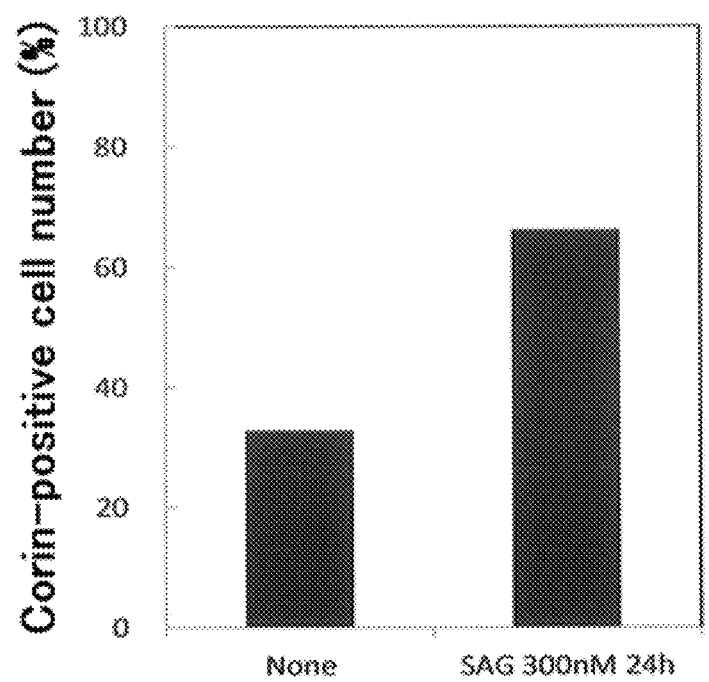
FIG. 2 is a graph showing the results of flow cytometry on cells of Day 12 cultured in the presence or absence of SAG (300 nM) in Example 1, namely the Corin-positive cell percentage (the percentage of the number of Corin-positive cells with respect to the total cell number).

Five days after the culture in Basal Medium A supplemented with 0.1 μM of LDN193189 and 3 μM CHIR99021, namely on the 12th day of the start of differentiation induction (Day 12), the cells were dissociated using TrypLE CTS, and suspended in $Ca^{2+}Mg^{2+}$-free HBSS (Invitrogen) supplemented with 2% FBS, 10 μM Y-27632 (WAKO), 20 mM D-glucose, and 50 μg/mL penicillin/streptomycin. The anti-Corin antibody was added to the suspension, and the resulting mixture was incubated at 4° C. for 20 minutes, the cells were sorted using FACS (BD) to collect Corin-positive cells, and the cell number was counted. The results of measurements of Corin-positive ratio are shown in FIG. 2. The left bar shows the Corin-positive ratio of the target cells when an undifferentiated state-maintaining culture is performed in the absence of SAG (preconditioning), and the right bar shows the same when an undifferentiated state-maintaining culture is performed in the presence of 300 nM of SAG (preconditioning).

As a result, it was found that the percentage of Corin-positive cells was increased by the treatment with SAG in a medium for maintaining undifferentiated state before differentiation induction.

Figure 3:
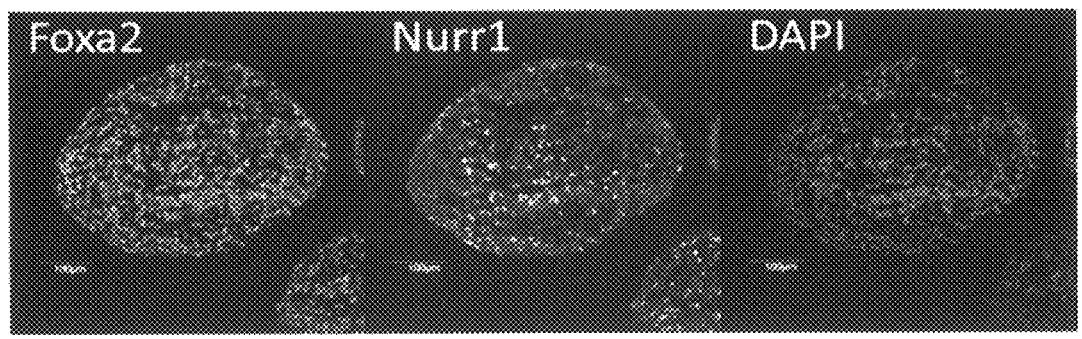
FIG. 3 is a figure (photograph) showing the results of examination whether or not a cell is differentiated into a dopaminergic neural progenitor cell by staining with Foxa2, or Nurr1 (both mesencephalic markers) with respect to cells of Day 28 in Example 1. With respect to the DAPI positive cells showing the presence of nucleus as 100%, the ratio was 99.0% for Foxa2, and 14.6% for Nurr1.

The collected Corin-positive cells were transferred to a PrimeSurface 96 U plate (Sumitomo Bakelite) in an amount of 20,000 cells/well, and subjected to suspension culture in Basal Medium B (Neurobasal medium (Invitrogen) supplemented with B27 Supplement without vitamin A (Invitrogen), 20 ng/mL BDNF, 10 ng/mL GDNF, 200 mM ascorbic acid, and 0.4 mM dbcAMP (Sigma)). In this suspension culture, medium supplemented with 30 μM of Y-27632 was used as the initial medium, but a half volume of the medium was replaced with a Y-27632-free medium once every three days. A suspension culture was performed until 16th day after sorting (Day 28), and the cells were stained with Foxa2, and Nurr1 (both are mesencephalic markers) to examine whether or not they were differentiated into dopaminergic neuron progenitor cells. As a result, as shown in FIG. 3, it was found that the obtained cells expressed Foxa2 and Nurr1. In this case, it was 99.0% for Foxa2 and 14.6% for Nurr1 with respect to DAPI-positive cells indicating the presence of nucleus as 100%.

Example 2

Similar to Example 1, experiments in which the concentration of SAG added was changed, and experiments in which A83-01 or LDN 193189 was added at the same time with SAG; were conducted, and the Corin-positive ratio were measured. The examination conditions and Corin-positive ratio under the respective conditions are shown in Table 1.

TABLE 1

| Conditions | Additive | Corin-Positive Rate (%) |
|---|---|---|
| Condition 2 | None (control) | 11.7 |
| Condition 3 | SAG (10 nM) | 22.7 |
| Condition 4 | SAG (300 nM) | 32.1 |
| Condition 5 | SAG (10 nM), A83-01 (500 nM) | 17.8 |
| Condition 6 | SAG (300 nM), A83-01 (500 nM) | 40.5 |
| Condition 7 | SAG (10 nM), LDN193189 (100 nM) | 26.9 |
| Condition 8 | SAG (300 nM), LDN193189 (100 nM) | 38.7 |
| Condition 9 | A83-01 (500 nM) | 12.4 |
| Condition 10 | LDN193189 (100 nM) | 12.6 |
| Condition 11 | A83-01 (500 nM), LDN193189 (100 nM) | 7.9 |

From the above results, it was found that when SAG is added, or A83-1 or LDN 193189 is added in addition to SAG, the Corin-positive ratio improves depending on the concentration of SAG added as compared with the control. On the other hand, when only A83-1 and/or LDN 193189 was added, no effect was exhibited.

Example 3

Production with iPS Cells Generated by Another Method

LPF 11, a human iPS cell, has been established by introducing Oct3/4, Sox2, Klf4, and L-MYC into human PBMC by a Sendai virus vector (Cytotune 2.0L, produced by ID Pharma Co., Ltd.), and culturing the same by the method according to the protocol published by Kyoto University (Establishment, maintenance culture of human iPS cells; CiRA Ff-iPSCprotocol JP v140310, //www.cira.kyoto-u.ac.jp/j/research/protocol.html) using StemFit medium (produced by Ajinomoto Healthy Supply Co., Inc. Inc.), and Laminin-511 E8 (produced by Nippi, Inc.).

Figure 4:
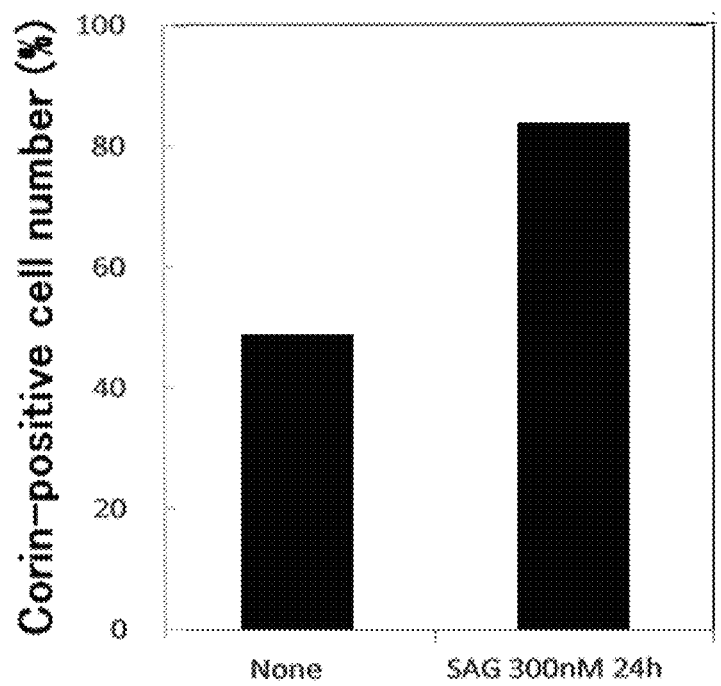
FIG. 4 shows the results of flow cytometry on Day 12 cells cultured in the presence or absence of SAG (300 nM) in Example 3, namely the percentage of the Corin-positive cells.

Using this iPS cell, culturing and differentiation induction were carried out in the same manner as in Example 1 and the percentage of the number of Corin-positive cells with respect to the total cell number was measured on the 12th day (Day 12) using an anti-Corin antibody. The results of measurements of Corin-positive ratio are shown in FIG. 4. The left bar shows the Corin-positive ratio when an undifferentiated state-maintaining culture is performed in the absence of SAG (preconditioning), and the right bar shows the Corin-positive ratio when an undifferentiated state-maintaining culture is performed in the presence of 300 nM of SAG (preconditioning).

As a result, as in the case of Example 1, it was found that the percentage of Corin-positive cells was increased by the treatment with SAG in a medium for maintaining undifferentiated state before differentiation induction, irrespective of the types of iPS cells.

Example 4

Cell Transplantation into Animal

It was investigated whether the cells (equivalent to Day 28) generated in Example 1 were suitable for transplantation. In this case, the medium was replaced in half every 3 days.

The cells of Day 28 were subjected to immunostaining with respect to TH (dopaminergic neural cell marker), Foxa2, and Nurr1 (both, mesencephalic markers). As a result, it was found as shown in FIG. 3 that the obtained cells expressed Foxa2, and Nurr1. In this case, it was 99.0% for FOX A2 and 14.6% for Nurr1 with respect to DAPI positive cells indicating the presence of nucleus as 100%.

Figure 5:
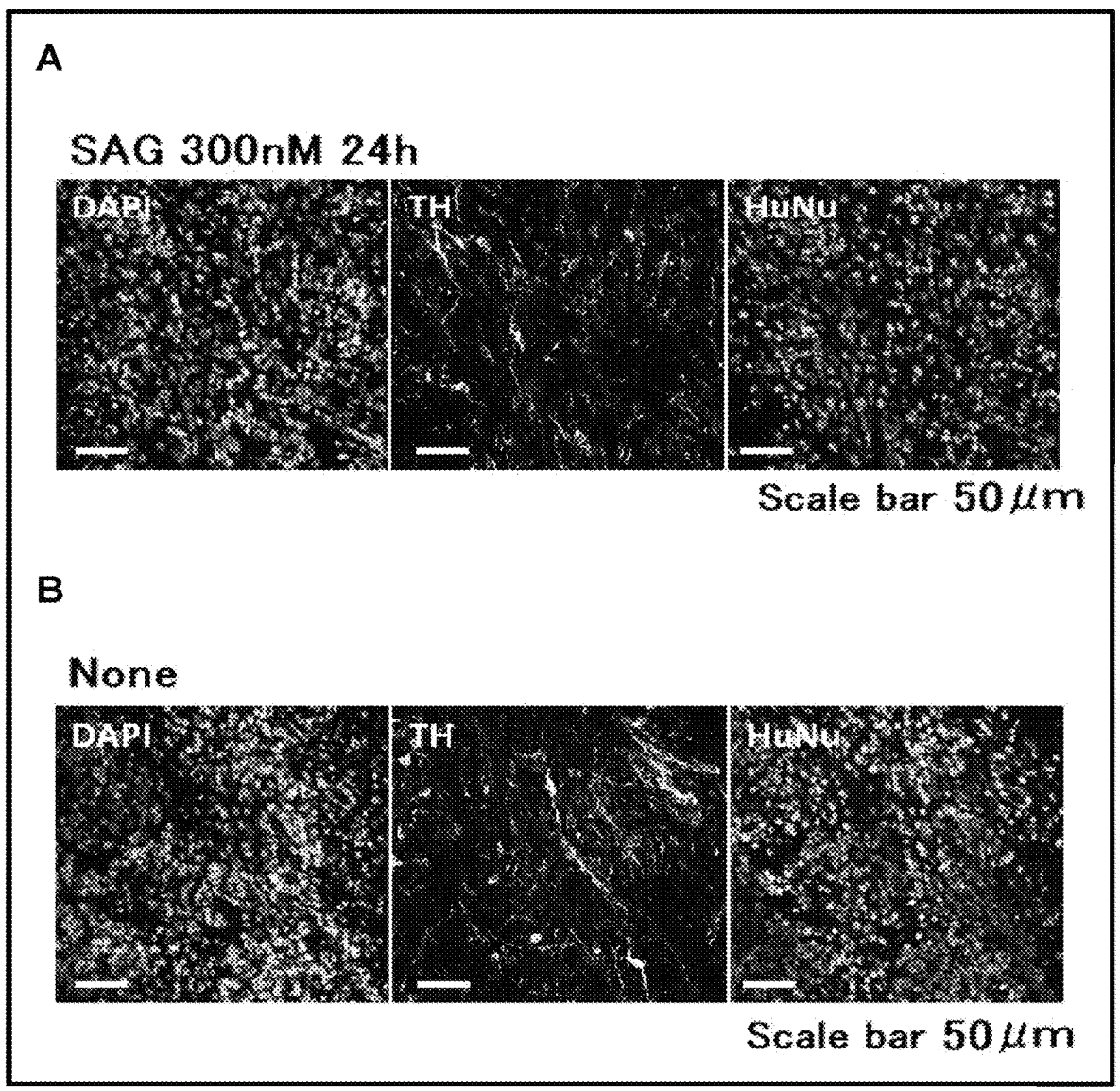
FIG. 5 shows the condition of a graft at 4 weeks after grafting cells of Day 28 to the rat brain (6-OHDA-administered rats) in Example 1. Namely, the figure (photographs) shows the results of examination whether or not a cell is differentiated into a dopaminergic neural progenitor cell by staining the graft with TH (mesencephalic marker), or HuNu (human cell nucleus). Panel A was for the graft of cells cultured in the presence of SAG (300 nM), and with respect to the HuNu-positive cells showing the presence of the grafted cells (human cell nucleus) as 100%, the TH-ratio was 9.24% on average (6.1% in individual (1), and 12.37% in individual (2)). Panel B was for the graft of cells cultured in the absence of SAG; and with respect to the HuNu positive cells as 100%, the TH-ratio was 9.7% on average (6.27% in individual (3), and 13.13% in individual (4)).

A plurality of cell aggregates containing $4 \times 10^5$ cells obtained as described above were suspended in 2 μL of physiological saline, and injected into the striatum of a model rat of Parkinson's disease (6-OHDA uni-laterally administered rat) using a 22 gauge injection needle, and the appearance of the graft after 4 weeks was observed (FIG. 5). Through an analysis of the graft, TH positive fibers and cell bodies were recognized (FIGS. 5A and B). In this case, between the SAG-treated cell graft and the non-treated cell graft there was no difference in terms of the ratio of the number of TH-positive cells to the number of HuNu-positive cells (human cell nucleuses, which shows survived cell number of grafted cells), and equal chromatic figures were observed (FIGS. 5A and B).

From the above results, survival of the graft and maturation to dopamine-producing cells of the cells (Day 28) produced in Example 1 with a SAG treatment or without a SAG treatment were confirmed, which shows that they are suitable as cells to be used for treatment of Parkinson's disease.

INDUSTRIAL APPLICABILITY

The present invention is useful for regenerative medicine, especially for treatment of Parkinson's disease.

What is claimed is:

1. A method for producing a cell population comprising Corin positive and/or Lrtm1 positive cells capable of differentiating into dopaminergic neuron progenitor cells, said method comprising:

(i) culturing human pluripotent stein cells (PSC) on a Laminin-511 E8 coated plate in a medium comprising a Sonic hedgehog (SHH) signal stimulant and bFGF for 6 to 48 hours to precondition and maintain the stem cells in an undifferentiated state, (ii) culturing the pluripotent stem cells obtained in step (i) the Laminin-511 E8 in a medium containing a BMP inhibitor and a TGF-beta inhibitor for at least one day;

(iii) replacing the medium from (ii) with a medium containing a BMP inhibitor, a TGF-beta inhibitor, a SHH signal-stimulating agent, and FGF8 and further culturing the cells for at least one day;

(iv) replacing the medium from (iii) with a medium containing a BMP inhibitor, a TGF-beta inhibitor, a SHH signal-stimulating agent, FGF8, and a GSK3β inhibitor and further culturing the cells for at least one day;

(v) replacing the medium from (iv) with a medium containing a BMP inhibitor and a GSK3β inhibitor and further culturing the cells for at least one day to produce a population of cells containing higher percentage of Corin- and/or leucine-rich repeats and transmembrane domains 1 (Lrtm1)-positive cells as compared to a population of Corin- and/or Lrtm1 positive cells produced from PSC that are not pre-conditioned in a medium comprising SHH signal-stimulating agent and bFGF, and;

wherein steps (ii)-(v) are performed for 10-21 days.

2. The method of claim 1 further comprising:

(vii) collecting Corin- and/or leucine-rich repeats and transmembrane domains 1 (Lrtm1)-positive cells from the cells obtained in (vi) using an antibody which binds to Corin and/or an antibody which binds to Lrtm1; and (viii) culturing the cells obtained in (vii) in suspension in a medium containing a neurotrophic factor for at least 7 days to produce dopaminergic neuron progenitor cells.

3. The method according to claim 1, wherein the SHH signal stimulant is SAG (N-methyl-N'-(3-pyridinylbenzyl)-N'-(3-chlorobenzo[b]thiophene-2-carbonyl)-1,4-diaminocyclohexane), shh protein or a fragment thereof, Purmorphamine, or a combination thereof.

4. The method according to claim 1, wherein the medium for maintaining undifferentiated state in (i) further comprises a TGFβ inhibitor or a BMP inhibitor.

5. The method according to claim 4, wherein the TGFβ inhibitor is A83-01, and the BMP inhibitor is LDN 193189.

6. The method according to claim 1, wherein the pluripotent stem cells are cultured for a period of about 18 to 28 hours in (i).

7. The method according to claim 1, wherein the medium in (ii) further comprises a ROCK inhibitor.

8. A method for producing dopaminergic neuron progenitor cells comprising:
(i) culturing human pluripotent stem cells (PSC) on a Laminin-511 E8 coated plate in a medium comprising a Sonic hedgehog (SHH) signal stimulating agent and bFGF for 6 to 48 hours to precondition and maintain the stem cells in an undifferentiated state,
(ii) culturing the pluripotent stern cells obtained in step (i) on the Laminin-511 E8 in a medium containing a BMP inhibitor and a TGF-beta inhibitor for at least one day:
(iii) replacing the medium from (ii) with a medium containing a BMP inhibitor, a TGF-beta inhibitor, a SHH signal-stimulating agent, and FGF8 and further culturing the cells for at least one day:
(iv) replacing the medium from (iii) with a medium containing a BMP inhibitor, a TGF-beta inhibitor, a SHH signal-stimulating agent, FGF8, and a GSK3β inhibitor and further culturing the cells for at least one day;
(v) replacing the medium from (iv) with a medium containing a BMP inhibitor and a GSK3β inhibitor and further culturing the cells for at least one day to produce a population of cells containing higher percentage of Corin- and/or leucine-rich repeats and transmembrane domains 1 (Lrtm1)-positive cells as compared to a population of Corin- and/or Lrtm1 positive cells produced from PSC that are not pre-conditioned in a medium comprising SHH signal-stimulating agent and bFGF; wherein steps (ii)-(v) are performed for 10-21 days; and
(vi) collecting Corin positive and/or Lrtm1 positive cells and culturing the Corin positive and/or Lrtm1 positive cells in a suspension culture in a medium comprising one or more neurotrophic factors to produce dopaminergic neuron progenitor cells.

9. The method according to claim 8, wherein the substance that binds to Corin or the substance that binds to Lrtm1 is an antibody or aptamer that binds to Corin or Lrtm1.

10. The method according to claim 8, wherein the neurotrophic factors are BDNF and GDNF.

11. The method according to claim 8, wherein the medium comprising a neurotrophic factor further comprises B27 Supplement, ascorbic acid, and a cAMP analog.

12. The method according to claim 11, wherein the cAMP analogue is Dibutyryl cyclic AMP.

* * * * *